(12) United States Patent
Mitsuhara et al.

(10) Patent No.: US 6,750,381 B2
(45) Date of Patent: *Jun. 15, 2004

(54) PATHOGEN-RESISTANT PLANTS TRANSFORMED WITH A DNA ENCODING SARCOTOXIN 1A LINKED TO A SIGNAL PEPTIDE AND A METHOD FOR PRODUCTION THEREOF

(75) Inventors: Ichiro Mitsuhara, Tsukuba (JP); Masahiro Ohshima, Tsukuba (JP); Yuko Ohashi, Tsukuba (JP)

(73) Assignee: National Institute of Agrobiological Sciences, Ibaraki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/805,813

(22) Filed: Feb. 26, 1997

(65) Prior Publication Data

US 2002/0166142 A1 Nov. 7, 2002

(30) Foreign Application Priority Data

Mar. 25, 1996 (JP) .............................. 8-068809
Jul. 17, 1996 (JP) .............................. 8-187763

(51) Int. Cl.$^7$ ........................... A01H 5/00; C12N 15/82

(52) U.S. Cl. ...................... 800/301; 800/279

(58) Field of Search ................. 800/279, 301, 800/205; 536/23.6, 23.7; 435/172.3, 320.1, 419

(56) References Cited

U.S. PATENT DOCUMENTS 5,538,525 A * 7/1996 Broekaert et al. .............. 47/58
5,597,945 A * 1/1997 Jaynes et al. ................ 800/205

FOREIGN PATENT DOCUMENTS

| CA | 2154019 | 1/1996 | ........... C12N/15/16 |
| EP | 0 448 511 A1 | 9/1991 | .......... A01N/63/00 |
| EP | 0 497 366 A2 | 8/1992 | ........... C07K/7/06 |
| EP | 0 552 559 A2 | 7/1993 | ........... C12N/15/62 |
| JP | 7-250685 | 10/1995 | |
| WO | WO 89/04371 | 5/1989 | ........... C12P/21/00 |
| WO | WO 90/11770 | 10/1990 | .......... A61K/37/102 |
| WO | WO 93/05153 | 3/1993 | ........... C12N/15/29 |

OTHER PUBLICATIONS

Stam M, et al. "The silence of genes in transgenic plants." Ann. Bot. 79: 3–12.*
Koziel MG, et al. "Optimizing expression of transgenes with an emphasis on post–transcriptional events." Plant Mol. Biol. 32: 393–405.*
Smith CJS, et al. "Antisense RNA inhibition of polygalacturonase gene expression in transgenic tomatoes." Nature 334: 724–726.*
Iijima et al., "Purification, characterization, and cDNA cloning of an antifungal protein from the hemolymph of Sarcophaga peregrina (flesh fly) larva," The Journal of Biological Chemistry 268(16):12055–12061 (1993).
Destefano–Beltran, Luis. et al. 1990. "Enhancing Bacterial and Fungal Disease Resistance in Plants: Application to Potato." Chap.15 in The Molecular and Cellular Biology of the Potato. Edited by Michael E. Vayda and William D. Park. Wallingford, United Kingdom, C.A. B. International.
Huang, Wenjin et al. "Cloning of T7 Lysozyme Gene and Construction of the Vector for Transgenic Plants Resistant to Bacterial Infection." Weishengwu Xuebao 34:261–265, 1994. [In Chinese with Chinese and English summaries.] Abstracted in Biological Abstracts, vol. 99, No. 4, Feb. 28, 1995, Ref. No. 53629.
XP 002049262, Expression of a Ceropin B lytic peptide analog in transgenic tobacco confers enhanced resistance to bacterial wilt caused by Pseudomonas solanacearum, Plant Science, 89:43–53 (Elsevier Scientific Publishers Ireland Ltd.) (1993).
XP–002062298, Database WPI, Section CH, Week 9548, Derwent Publications Ltd., London, GB, "Express. Cassette Express. Antimicrobial peptide Creation Antimicrobial Plant Express.Peptide Derivative Insect," AN 95–370474; JP 07 250 685 A (Norinsuisansho Nogyo Seibutsu Shigen) (Oct. 3, 1995), abstract.
XP–002062299, Database WPI, Section CH, Week 9022, Derwent Publications Ltd., London, G.B., "Production of useful proteins—using genes of proteins specific to infection," AN 90–168365; JP 02 109 992 A (Norinsho KK) (Apr. 23, 1990), abstract.
XP–002062300, Database WPI, Section Ch, Week 9423, Derwent Publications Ltd., London, G.B., "Expression of heterologous peptide)s) in plants—comprises transforming plant cells with fusion gene encoding heterologous peptide fused to detectable marker protein," AN 94–187941; JP 06 125 782 A (Toa Gosei Chem. Ind. Ltd.) (May 10, 1994), abstract.
XP–002029836, "Small Cysteine–Rich Antifungal Proteins from radish: Their Role in Host Defense," The Plant Cell., vol. 7, 573–588 (May 1995), The American Society of Plant Physiologists.

(List continued on next page.)

Primary Examiner—Amy J. Nelson
Assistant Examiner—Anne Kubelik
(74) Attorney, Agent, or Firm—Townsend and Townsend and Crew LLP

(57) ABSTRACT

The present invention is drawn to a method of conferring resistance to pathogenic fungi on a plant by transformation with a nucleic acid encoding Sarcotoxin 1a operatively linked to a signal peptide, and optionally linked via the hinge region of tobacco chitinase to a plant peptide, and plants thereby obtained.

16 Claims, 15 Drawing Sheets

OTHER PUBLICATIONS

Figure 1:
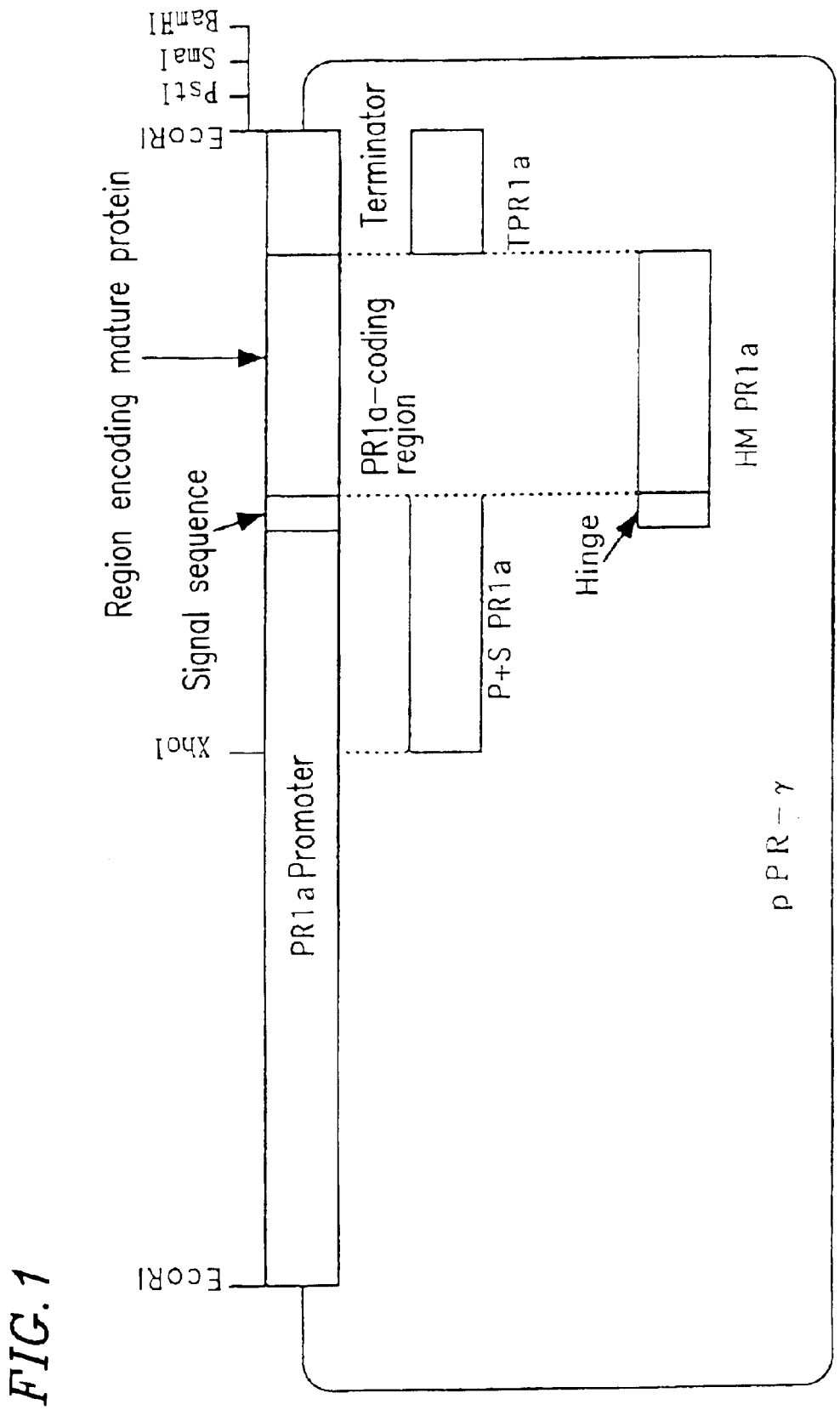

Matsumoto, Noriko, et al. (1986) "Molecular cloning of a cDNA and assignment of the C-terminal of sarcotoxin IA, a potent antibacterial protein of *Sarcophaga peregrina*", *Biochem. J.*, 239:717–722.

Matsufuru, H., et al. (1996) "Introduction of chimeric gene for an inducible fusion protein of Sarcotoxin 1A and PR–1a, and development of resistance against pathogen infection in the transgenic tobacco plants", *Extended Abstracts of the Annual Meeting of the Phytopathological Society of Japan*, 106:3–40.

* cited by examiner

FIG.3

Part of Sarcotoxin gene
(Region encoding C-terminal of mature peptide)

```
        Ala Ala Thr Ala Arg Gly ***
5'- GCT GCT ACA GCC AGA GGT TAA TTG AAA -3'
```

Part of sequence of PR1a gene
(Region encoding C-terminal of mature protein)

```
        Pro Tyr ***
5'- CCA TAC TAA TTG AAA CGA CCT ACG TCC ATT-3'
```

```
5'- GCT GCT ACA GCA CGT GGT TAA TTG AGC TCG AAA CGA CCT ACG TCC -3'
                    PmaCI            SacI
    ← TPR1aS1
```

FIG. 4

Part of sequence of PR1a gene
(Border between signal sequence and region encoding mature protein)

──── Signal sequence ──── | ──── Mature protein ────→

```
    Leu Phe Leu Val Ile Ser His Ser Lys Arg Ala Glu
5'-TTA TTC CTA GTA ATA TCC CAC TCT TGC CGT GCC CAA-3'
```

Part of Sarcotoxin gene
(Region encoding N-terminal of mature peptide)

```
                              Gly Trp Leu Lys Lys Ile Gly Lys Lys
                          5'-GGT TGG TTG AAA AAG ATT GGC AAA AAA-3'
```

```
     His Ser Lys Arg Ala Gly Trp Leu Lys Lys Ile Gly
5'-CAC TCC TGC AGA GCC GGT TGG TTG AAA AAG ATT GGC-3'
            PstI                                      ← MSARCO51
```

FIG. 5

Part of Sarcotoxin gene
(Region encoding C-terminal of mature peptide)

```
        Ala  Ala  Thr  Ala  Arg  Gly  ***
   5'-GCT  GCT  ACA  GCC  AGA  GGT  TAA  TTG-3'
   3'-CGA  CGA  TGT  CGG  TCT  CCA  ATT  AAC-5'

3'-CGA  CGA  TGT  CGT  GCA  CCA  ATT  AAC  TCG  AGC  TTT-5'
                       PmaCI                  SacI        ↑
                                                          |
                                                      MSARCO31
```

Direction of binary vector pTRA415 is changed

F.oxy.F-3

| Added amount of Sarcotoxin μg/ml | Culture time [h] | | | | |
|---|---|---|---|---|---|
| | 0 | 12 | 24 | 36 | 48 |
| 0 | 0.0707828 | 0.283131 | 0.786475 | 1.3291428 | 2.2729128 |
| 0 | 0.0707828 | 0.1966188 | 0.786475 | 1.3291428 | 2.2729128 |
| 0 | 0.0707828 | 0.283131 | 0.9516348 | 1.541491 | 2.548179 |
| 50 | 0.0707828 | 0.283131 | 0.786475 | 1.7695688 | 2.548179 |
| 50 | 0.0707828 | 0.283131 | 0.786475 | 1.541491 | 2.2729128 |
| 50 | 0.0707828 | 0.1966188 | 0.503344 | 1.132524 | 1.7695688 |
| 200 | 0.0707828 | 0.283131 | 0.786475 | 1.541491 | 2.2729128 |
| 200 | 0.0707828 | 0.1966188 | 0.503344 | 0.9516348 | 1.7695688 |
| 400 | 0.0707828 | 0.283131 | 0.786475 | 1.3291428 | 2.013376 |
| 400 | 0.0707828 | 0.283131 | 0.6370448 | 0.9516348 | 1.541491 |

Standard deviation

| Added amount of Sarcotoxin μg/ml | Culture time [h] | | | | |
|---|---|---|---|---|---|
| | 0 | 12 | 24 | 36 | 48 |
| 0 | 0 | 0.0499479 | 0.095355 | 0.1225993 | 0.158925 |
| 50 | 0 | 0.0499479 | 0.1634658 | 0.3227743 | 0.3948334 |
| 200 | 0 | 0.0611734 | 0.2002039 | 0.4170914 | 0.355918 |
| 400 | 0 | 0 | 0.1056631 | 0.2669385 | 0.3336731 |

Average

| Added amount of Sarcotoxin μg/ml | Culture time [h] | | | | |
|---|---|---|---|---|---|
| | 0 | 12 | 24 | 36 | 48 |
| 0 | 0.0707828 | 0.2542936 | 0.8415283 | 1.3999255 | 2.3646682 |
| 50 | 0.0707828 | 0.2542936 | 0.692098 | 1.4811946 | 2.1968868 |
| 200 | 0.0707828 | 0.2398749 | 0.6449095 | 1.2465629 | 2.0212408 |
| 400 | 0.0707828 | 0.283131 | 0.7117599 | 1.1403888 | 1.7774335 |

R.sola.AG-4 1272

| Added amount of Sarcotoxin μg/ml | Culture time [h] 0 | 6 | 11 | 13 |
|---|---|---|---|---|
| 0 | 0.07078275 | 0.38537275 | 1.541491 | 2.548179 |
| 0 | 0.07078275 | 0.38537275 | 2.013376 | 2.408579688 |
| 0 | 0.07078275 | 0.38537275 | 2.013376 | 2.548179 |
| 50 | 0.07078275 | 0.38537275 | 0.786475 | 0.709793688 |
| 50 | 0.07078275 | 0.63704475 | 1.541491 | 2.013376 |
| 200 | 0.07078275 | 0.38537275 | 0.503344 | 0.63704475 |
| 200 | 0.07078275 | 0.38537275 | 0.786475 | 0.786475 |
| 400 | 0.07078275 | 0.38537275 | 0.503344 | 0.568228188 |
| 400 | 0.07078275 | 0.38537275 | 0.786475 | 0.709793688 |

Standard deviation

| Added amount of Sarcotoxin μg/ml | Culture time [h] 0 | 6 | 11 | 13 |
|---|---|---|---|---|
| 0 | 0 | 0 | 0.272442932 | 0.080597701 |
| 50 | 0 | 0.177958978 | 0.533876934 | 0.921771893 |
| 200 | 0 | 0 | 0.20020385 | 0.105663143 |
| 400 | 0 | 0 | 0.20020385 | 0.100101925 |

Average

| Added amount of Sarcotoxin μg/ml | Culture time [h] 0 | 6 | 11 | 13 |
|---|---|---|---|---|
| 0 | 0.07078275 | 0.38537275 | 1.856081 | 2.501645896 |
| 50 | 0.07078275 | 0.51120875 | 1.163983 | 1.361584844 |
| 200 | 0.07078275 | 0.38537275 | 0.6449095 | 0.711759875 |
| 400 | 0.07078275 | 0.38537275 | 0.6449095 | 0.639010938 |

R.sola. Rhizoctonia solani

| Added amount of Sarcotoxin μg/ml | Culture time [h] | | |
|---|---|---|---|
| | 0 | 6 | 18 |
| 0 | 0.07078275 | 0.38537275 | 2.83917475 |
| 0 | 0.07078275 | 0.503344 | 3.46835475 |
| 0 | 0.07078275 | 0.283131 | 2.548179 |
| 50 | 0.07078275 | 0.503344 | 2.013376 |
| 50 | 0.07078275 | 0.503344 | 1.32914275 |
| 200 | 0.07078275 | 0.38537275 | 1.132524 |
| 200 | 0.07078275 | 0.63704475 | 1.32914275 |
| 400 | 0.07078275 | 0.283131 | 0.503344 |
| 400 | 0.07078275 | 0.503344 | 0.63704475 |

Standard deviation

| Added amount of Sarcotoxin μg/ml | Culture time [h] | | |
|---|---|---|---|
| | 0 | 6 | 18 |
| 0 | 0 | 0.110200088 | 0.470331339 |
| 50 | 0 | 0 | 0.483825971 |
| 200 | 0 | 0.177958978 | 0.139030451 |
| 400 | 0 | 0.155714106 | 0.094540707 |

Average

| Added amount of Sarcotoxin μg/ml | Culture time [h] | | |
|---|---|---|---|
| | 0 | 6 | 18 |
| 0 | 0.07078275 | 0.390615917 | 2.951902833 |
| 50 | 0.07078275 | 0.503344 | 1.671259375 |
| 200 | 0.07078275 | 0.51120875 | 1.230833375 |
| 400 | 0.07078275 | 0.3932375 | 0.570194375 |

PATHOGEN-RESISTANT PLANTS TRANSFORMED WITH A DNA ENCODING SARCOTOXIN 1A LINKED TO A SIGNAL PEPTIDE AND A METHOD FOR PRODUCTION THEREOF

BACKGROUND OF THE INVENTION

1. Field of the Invention

The present invention relates to a method for efficiently producing a useful foreign protein in a plant. The present invention also relates to a method for expressing a foreign protein in a plant so as to provide the plant with a new property, and to the breeding of a plant. More specifically, the present invention relates to a plant containing a gene encoding an anti-bacterial peptide derived from a Diptera insect and which confers resistance to bacterial and fungal pathogens.

2. Description of the Related art

In the past, it has been reported that when a foreign gene is introduced into the nucleus of a plant cell, the productivity of a peptide, which is a foreign gene product, is at most 0.1% to 0.3% of the total proteins. Particularly, in the case where the product of the foreign gene is a small peptide (hereinafter, referred to as "a short peptide") with a molecular weight of 7,000 or less, the product is likely to be degraded in a plant and is difficult to be accumulated in a great amount. Thus, there has been a demand for a method for efficiently expressing a short peptide.

When a foreign gene is introduced and expressed in a plant, a constitutive promoter, which is constantly expressed, such as the CaMV 35S promoter is mostly used. However, some possibilities are considered; for example, this expression method using the constitutive promoter may impose a burden at least on the plant's ability to produce a protein and the expressed protein may adversely affect the plant. In fact, attempts to produce a protein encoded by a gene that affects the growth of a plant, such as a gene involved in the synthesis of a plant hormone, often result in failures. This adverse tendency is especially outstanding when one attempts to increase the productivity of the protein encoded by the gene introduced into the plant.

On the other hand, a study has been made on a technique for introducing a gene encoding an anti-bacterial peptide into a plant and expressing the anti-bacterial peptide so as to provide the plant with resistance to bacteria. In particular, it has been disclosed in Japanese Laid-Open Patent Publication No. 7-250685 that Sarcotoxin 1*a*, which is an anti-bacterial peptide derived from a Diptera insect, was expressed in a plant in such a manner that the plant obtained anti-bacterial properties. However, since a short peptide such as Sarcotoxin 1a is expected to be unstable in plants, it is necessary to stabilize the peptide by producing it as a fusion protein with PR-1a which is an pathogenesis related protein of tobacco.

Furthermore, no plants have been discovered that produce an anti-bacterial peptide derived from a Diptera insect having anti-fungal activity, and confer resistance to pathogenic fungi.

SUMMARY OF THE INVENTION

According to the present invention, a plant which confers resistance to pathogenic fungi, includes a gene encoding an anti-bacterial peptide.

In one embodiment of the present invention, the pathogenic fungi are *Rhizoctonia solani, Pythium aphanidermatum*, and *Phytophthora infestans.*

In another embodiment of the present invention, the anti-bacterial peptide is derived from the Diptera insect.

In another embodiment of the present invention, the anti-bacterial peptide derived from the Diptera insect is Sarcotoxin 1a.

In another embodiment of the present invention, a gene encoding the anti-bacterial peptide derived from the Diptera insect is introduced into a plant in a form selected from the group consisting of: a recombinant gene containing the gene encoding the anti-bacterial peptide derived from the Diptera insect; an expression cassette in which the recombinant gene is bound to a plant promoter; and an expression vector composed of the expression cassette and a drug resistant gene linked to a plant promoter which is constitutively expressed.

In another embodiment of the present invention, the recombinant gene which encodes the anti-bacterial peptide derived from the Diptera insect is bound to a plant gene via a hinge region of tobacco chitinase.

In another embodiment of the present invention, the Sarcotoxin 1a is bound to a signal sequence of a plant protein.

In another embodiment of the present invention, the plant promoter is the inducible promoter of the tobacco PR-1a gene.

In another embodiment of the present invention, the expression cassette has a terminator derived from the tobacco PR-1a gene.

In another embodiment of the present invention, the expression vector further has a T-DNA region and a drug resistant gene.

In another embodiment of the present invention, the drug resistant gene is expressed by the Cauliflower mosaic virus 35S promoter.

According to the present invention, a plant with resistance to pathogenic bacteria, includes a gene selected from the group consisting of: a recombinant gene in which a gene encoding an anti-bacterial peptide is bound to a plant gene via a hinge region of tobacco chitinase, an expression cassette in which the recombinant gene is bound to a plant promoter, and a gene having the expression cassette and a drug resistance gene linked to a plant promoter which is constitutively expressed.

In one embodiment of the present invention, the pathogenic bacteria is *Pseudomonas syringae* pv. *tabaci* or *Erwinia carotovora* subsp. *carotovora.*

In another embodiment of the present invention, the anti-bacterial peptide is Sarcotoxin 1a derived from a Diptera insect.

According to the present invention, a recombinant gene, in which a gene encoding an anti-bacterial peptide is bound to a plant gene via a hinge region of tobacco chitinase gene, is provided.

In one embodiment of the present invention, the gene encoding an anti-bacterial peptide is a gene encoding an anti-bacterial peptide derived from the Diptera insect.

In another embodiment of the present invention, the anti-bacterial peptide derived from the Diptera insect is Sarcotoxin 1a.

In another embodiment of the present invention, an expression cassette, in which the above-mentioned recombinant gene is bound to a plant promoter, is provided.

In another embodiment of the present invention, an expression vector for introducing the above-mentioned expression cassette into a plant is provided.

According to the present invention, a plant which confers resistance to pathogenic fungi and bacteria, includes a gene encoding a peptide which has anti-fungal and anti-bacterial activity.

The gene encoding the fusion protein of the present invention was introduced into a plant with the expression vector and expressed. As a result, the fusion protein was constitutively produced, and the productivity thereof increased by the induction of salicylic acid or the like. In addition, the fusion protein was cleaved at its linked site by the proteolytic activity of an unidentified protein which was induced by salicylic acid and TMV infection. This led to the induction of producing the respective free proteins from the fusion protein.

By using the recombinant gene, the expression cassette, or the expression vector of the present invention, a foreign protein can be constitutively produced as a fusion protein and the respective free proteins can be produced. Furthermore, the anti-bacterial peptide is expressed as a fusion protein with a plant gene by the method of the present invention, and thus, it is possible to obtain a plant which confers resistance to pathogenic fungi as well as pathogenic bacteria.

Thus, the invention described herein makes possible the advantages of (1) increasing the stability of a target foreign protein (peptide) in a plant by expressing the foreign protein as a fusion protein with other proteins; (2) providing an expression cassette or an expression vector containing the expression cassette, wherein the expression cassette expresses a recombinant gene encoding the fusion protein at a constitutively constant level, and the expression level inductively increases, thereby increasing the productivity of a foreign protein in a plant; (3) cleaving proteins once expressed as a fusion protein at its fusion site under an induced condition to produce the respective free proteins; (4) providing a plant transformed by using the expression cassette or expression vector; and (5) providing a plant which confers resistance to pathogens by using a protein having anti-bacterial and anti-fungal activity.

These and other advantages of the present invention will become apparent to those skilled in the art upon reading and understanding the following detailed description with reference to the accompanying figures.

BRIEF DESCRIPTION OF THE DRAWINGS

FIG. 1 shows a plasmid pPR-γ having a genomic clone of the tobacco PR-1a gene.

FIG. 2 shows a sequence of a primer SPR-1a31 (SEQ ID NO: 2). Part of sequence of PR1a gene in the periphery of 3' end of signal sequence=SEQ ID NOS: 10 and 11.

FIG. 3 shows a sequence of a primer TPR-1a51 (SEQ ID NO: 15). Part of sarcotoxin gene region encoding C-terminal of mature peptide SEQ ID NOS: 12 and 13. Part of sequence of PR1a gene region encoding C-terminal of mature protein=SEQ ID NO: 4.

FIG. 4 shows a sequence of primer MSARCO51 (SEQ ID NO: 8). Part of sequence of PR1a gene border between signal sequence and region encoding mature protein=SEQ ID NOS: 10 and 11. Part of sarcotoxin gene region encoding N-terminal of mature peptide=SEQ ID NOS: 16 and 17.

FIG. 5 shows a sequence of a primer MSARCO31 (SEQ ID NO: 8). Part of sarcotoxin gene region encoding C-terminal of mature peptide=SEQ ID NOS: 19 and 13.

FIG. 6 schematically illustrates the construction of a recombinant gene of the present invention.

FIG. 7 shows the binary vectors pTRA415 and pTRA415 (R).

FIG. 8 shows the plasmids PSS, PSP, and PST10 used in the present invention.

FIG. 9 shows the production of Sarcotoxin in a plant transformed with PSP and PST10. The fusion protein is detected by western blotting using the anti-Sarcotoxin antibody or the anti-PR-1a antibody.

FIG. 10 shows the resistance against *P. syringae* pv. *tabaci* infection in a transgenic plant.

FIG. 11 shows the resistance against *E. carotovora* subsp. *carotovora* infection in a transgenic plant.

FIG. 12 shows an anti-*Fusarium oxysporum* F-3 activity of Sarcotoxin 1a in vitro.

FIG. 13 shows an anti-*Rhizoctonia solani* AG-4 1272 activity of Sarcotoxin 1a in vitro.

FIG. 14 shows an anti-*Rhizoctonia solani* activity of Sarcotoxin 1a in vitro.

FIG. 15 shows the resistance against *Phytophthora infestans* infections in a transgenic plant.

DESCRIPTION OF THE PREFERRED EMBODIMENTS

Hereinafter, the present invention will be described in detail.

The present invention relates to a recombinant gene in which a foreign gene is linked to a plant gene via a hinge region of tobacco chitinase, an expression cassette in which a plant promoter is linked to a recombinant gene, and an expression vector for introducing this expression cassette into a plant.

The term "plant" as used herein includes monocotyledon and dicotyledon. Examples of particularly preferable plants include tobacco, citrus fruit, Chinese cabbage, lettuce, peach, rice, potato, tomato, barley, wheat, and apple.

The term "plant promoter" as used herein refers to a promoter expressed in a plant. Examples of the plant promoter include, but are not limited to, promoters whose expression is induced by a certain kind of stress, e.g., the promoter of an pathogenesis related protein PR-1a of tobacco (hereinafter, referred to as "the tobacco PR-1a promoter"), the Cauliflower mosaic virus 35S promoter (hereinafter, referred to as "the CaMV 35S promoter"), the promoter of nopaline syntase, and the like. An enhancer can be used for high expression. As the enhancer, an enhancer region containing a sequence upstream of the 35S promoter is preferable. A plurality of enhancers can be used.

The term "plant gene" as used herein refers to a gene of a plant. As the plant gene, any genes can be used. Preferably, examples of the plant gene include an pathogenesis related protein PR-1a gene of tobacco. However, the plant gene is not limited thereto.

The term "hinge region of tobacco chitinase" as used herein refers to a region partitioning different functional regions (i.e., a chitin binding region and a catalytic region) in a tobacco chitinase protein (H. Shinshi et al., Plant Mole. Biol. vol. 14, pp. 357–368 (1990)). Due to the presence of the hinge region of tobacco chitinase at a link portion between plant genes, it is expected to prevent steric hindrance of each protein.

The term "foreign gene" as used herein refers to a gene encoding a protein that is heterogenous to a host plant. As the foreign gene, genes of plants, genes of microorganisms such as bacteria and yeast, genes of insects, genes of animals, and the like can be preferably used. When pathogen resistant plants are bred, a gene encoding an anti-microbial peptide can be used as a foreign gene. Examples of such a foreign gene include, but are not limited to, genes encoding an anti-bacterial peptide derived from a Diptera insect. As the anti-bacterial peptide derived from the Diptera insect, Sarcotoxin 1a derived from *Boettherisca peregrina*, Sapecin, or an anti-fungal peptide are preferable. However, the anti-microbial peptide is not limited thereto. A fusion protein can also be secreted when a signal sequence is added to a foreign gene introduced into an expression cassette.

Conventional gene recombinant techniques can be used for producing the above-mentioned recombinant gene in which a foreign gene is linked to a plant gene via a hinge region of tobacco chitinase.

The term "expression cassette" as used herein refers to a nucleic acid sequence in which the recombinant gene and various regulatory elements regulating the expression of the recombinant gene, e.g., a promoter, an enhancer, and the like are operably linked to each other in a host cell in such a manner that the recombinant gene may be expressed. The expression cassette can be constructed in accordance with a conventional method. An appropriate promoter, e.g., the tobacco PR-1a promoter is linked to the recombinant gene. The tobacco PR-1a promoter is known to be inducible and expressed at a high level. More preferably, a terminator can be linked to the recombinant gene.

The term "terminator" as used herein refers to a sequence which is involved in the termination of transcription of DNA into mRNA and the addition of a poly A sequence, and which is positioned downstream of a region of a gene encoding a protein. The terminator is known to be involved in the stability of mRNA and affect the expression level of a gene. Although not limited, examples of the terminator include a Cauliflower mosaic virus 35S terminator, a terminator of the nopaline syntase gene, and a terminator of the tobacco PR-1a gene. It has been confirmed that the terminator of the tobacco PR-1a gene increases expression efficiency of a gene.

The term "expression vector" as used herein refers to a type of vector transferring the expression cassette to a host cell. It is well-known to those skilled in the art that the type of an expression vector and the kind of a regulatory element to be used can vary depending upon a host cell. The expression vector of the present invention can further have a T-DNA region and a drug resistant gene.

It is desirable that the drug resistant gene enables a transgenic plant to be easily selected. As the drug resistant gene, the neomycin phosphotransferase II (NPTII) gene, a hygromycine phosphotransferase gene, and the like are preferably used.

Although not limited, examples of the promoter expressing the drug resistant gene include the above-mentioned plant promoters such as the tobacco PR-1a promoter, the CaMV 35S promoter, and the nopaline syntase promoter, and the like. Preferably, the CaMV 35S promoter which is constitutively expressed at a high level is used. When the inducible tobacco PR-1a promoter is used as a promoter for allowing the expression cassette to express a foreign gene, the inducible PR-1a promoter is constitutively expressed under the effect of the CaMV 35S promoter, and the expression level of the PR-1a promoter is increased by salicylic acid or the formation of necrotic lesions caused by pathogen infection. The reason for this is as follows: The CaMV 35S promoter and the PR-1a promoter are positioned adjacent to each other, so that the properties of the PR-1a promoter are affected by a cis-element on the 35S promoter.

As a vector used for constructing an expression vector, a pBI-type vector, a pUC-type vector, or a pTRA-type vector are preferably used. The pBI-type vector can introduce an expression cassette into a plant through a binary vector-type or intermediate vector-type Agrobacterium. Examples of the pBI-type vector include pBI121, pBI101, pBI101.2, pBI101.3, and the like. The pUC-type vector can introduce an expression cassette directly into a plant. Examples of the pUC-type vector include pUC18, pUC19, pUC9, and the like. Herein, a pTRA-type binary vector (Ohshima et al., Plant Cell, vol. 2, pp. 95–106 (1990)) can be preferably used. This expression vector includes an expression cassette containing a fusion gene with a region (T-region) which may be introduced into a plant, and the NPT gene which is expressed under the control of the CaMV 35S promoter as a marker gene.

In the case where the expression vector of the present invention has a T-region, the structure of the T-region has the following characteristics:

(1) The expression cassette containing a foreign gene on the right side of the T-region can be positioned in such a manner that, when the expression vector is mobilized from Agrobacterium to a plant, the foreign gene to be introduced into the plant is mobilized, followed by the marker gene transfer. Because of this, the transgenic plants, selected based on their drug resistance, are highly likely to contain a foreign gene; and (2) The CaMV 35S promoter controlling the expression of the marker gene and the PR-1a gene promoter controlling the expression of the foreign gene are positioned adjacent to each other. Although normally the use of the PR-1a promoter is hardly expected to allow the expression of a foreign gene under non-induced conditions, the arrangement of the CaMV 35S promoter and the PR-1a promoter allows a constitutive expression to occur (presumably under the effect of the CaMV 35S promoter) and allows a high expression level.

When the PR-1a promoter is used, the expression vector induces the expression of a foreign gene at a high level by salicylic acid or the formation of necrotic lesions caused by pathogen infection.

The expression vector of the present invention can be produced by using gene recombinant techniques known to those skilled in the art.

Methods known to those skilled in the art can be used for introducing a recombinant gene, an expression cassette, or an expression vector into a plant cell.

The expression cassette or the expression vector obtained in the above-manner is introduced through Agrobacterium or directly into a cell. As the method using Agrobacterium, for example, a method of Nagel et al. (Microbiol. Lett., 67, 325 (1990)) can be used. According to this method, for example, Agrobacterium is first transformed with an expression vector by electroporation, and then transformed Agrobacterium is introduced into a plant cell by a method described in the Plant Molecular Biology Manual (S. B. Gelvin et al., Academic Press Publishers). As the method for directly introducing an expression cassette or an expression vector into a cell, an electroporation method and a gene gun method can be suitably used.

The cells, introduced into an expression cassette or an expression vector, are then subjected to a selection process based on drug resistance such as kanamycin resistance. Thereafter, the cells can be regenerated as a plant by a conventional method.

In order to confirm the expression of a foreign gene in the transgenic plant, a method well known to those skilled in the art can be used. For example, a soluble protein can be extracted from the transgenic plant; the extracted protein is separated by SDS-PAGE as described in Analytical Biochemisty 166, 368–379 and transferred to a PVDF membrane. Then, the protein is immunologically detected, whereby the expression of the protein is confirmed.

It can be determined whether or not a plant transformed with a gene encoding an anti-bacterial peptide derived from a Diptera insect of the present invention confers resistance to pathogenic bacteria in the following manner. Leaves of a transgenic plant and those of a control plant are inoculated with bacterial pathogens by using a bundle of needles. The size of necrotic lesions and the changes in color of the leaves are observed after an appropriate period of time (after 6 days in the present invention) and the degree of disease symptom is determined based on the size of necrotic lesions and the changes in color of the leaves. Examples of the bacterial pathogens include *P. syringae* pv. *tabaci* and *E. carotovora* subsp. *carotovora*, and the like.

It can be determined whether or not a plant transformed with a gene encoding an anti-bacterial peptide derived from a Diptera insect of the present invention confers resistance to pathogenic fungi in the following manner. Transgenic plants and control plants are self-pollinated, respectively and the seeds thus obtained are germinated under drug resistance selection to obtain young plants. Agar media, in which the respective young plants are grown, are inoculated with bacterial pathogens and green individuals which still exist after an appropriate period of time of inoculation are judged as resistant plants. Examples of the fungal pathogens include *Fusarium oxysporum* F-3, *Rhizoctonia solani*, *Rhizoctonia solani* AG-4 1272, *Pythium aphanidermatum*, and the like.

As one embodiment of the present invention, a recombinant gene will be described, in which a plant gene (e.g., the tobacco PR-1a protein gene) is linked to an anti-bacterial peptide derived from a Diptera insect (e.g., a gene of Sarcotoxin 1a) as a foreign gene via a hinge region.

Sarcotoxin 1a is a peptide which widely exhibits antibacterial properties to bacteria. It has been confirmed that Sarcotoxin 1a is introduced into a tobacco plant to allow a plant which confers a certain resistance to bacterial pathogens to be produced (Japanese Laid-Open Patent Publication No. 7-250685). However, since a short peptide such as Sarcotoxin 1a is expected to be unstable in a plant, it is required to stabilize the peptide by producing it as a fusion protein with PR-1a which is pathogenesis-specific protein of tobacco. The hinge region of tobacco chitinase partitions different functional regions (a chitin binding region and a catalytic region) in a tobacco chitinase. Due to the presence of the hinge region of tobacco chitinase at a link site between tobacco PR-1a proteins, it is expected to prevent steric hindrance of peptide. Furthermore, a signal sequence of the tobacco PR-1a protein is added to an N-terminal of a fusion protein, whereby the fusion protein can be secreted. As a result, anti-microbial properties of a plant against pathogens are expected to improve. This is because the secretion of the fusion protein into the interstices of plant cells may prevent damage against the plant cells and may prevent bacterial pathogens from invading through the cell interstices.

Hereinafter, the present invention will be described by way of illustrative examples. A restriction enzyme, a plasmid, and the like used in the following examples are available from Takara Shuzo Co., Ltd. and Toyobo Co., Ltd.

EXAMPLE 1

Construction of a Recombinant Gene and an Expression Cassette

A recombinant gene in which a foreign gene is linked to a plant gene via a hinge region of tobacco chitinase was constructed in the following manner. The construction method will be described with reference to FIG. 1.

(1) Preparation of a P+S PR-1a Fragment (a DNA Fragment Having a Sequence Encoding a Part of the PR-1a Promoter and the Signal Peptide of the PR-1a Protein)

A region of the PR-1a promoter (3' portion from an XhoI site) and a sequence encoding a signal peptide were amplified, using a plasmid pPR-γ (M. Oshima et al., FEBS Letters vol. 255, pp. 243–246 (1987)) having a genomic clone of the tobacco PR-1a gene shown in FIG. 1 as a template, thereby obtaining a DNA fragment (P+S PR-1a fragment). The P+S PR-1a fragment was obtained by PCR using Pfu polymerase (Stratagene, La Jolla, Calif.), and primers PR-1a51 (SEQ ID NO. 1) and SPR-1a31 (SEQ ID NO. 2). Although the primer SPR-1a31 has a sequence complementary to the sequence encoding a signal peptide of the PR-1a gene, its base is partially substituted as shown in FIG. 2. By substitution of the base, a restriction enzyme Pst1 site is newly introduced; however, there is no change in the amino acid sequence of the signal peptide.

(2) Preparation of a TPR-1a Fragment (a DNA Fragment Having a Terminator Region of the PR-1a Gene)

Figure 2:
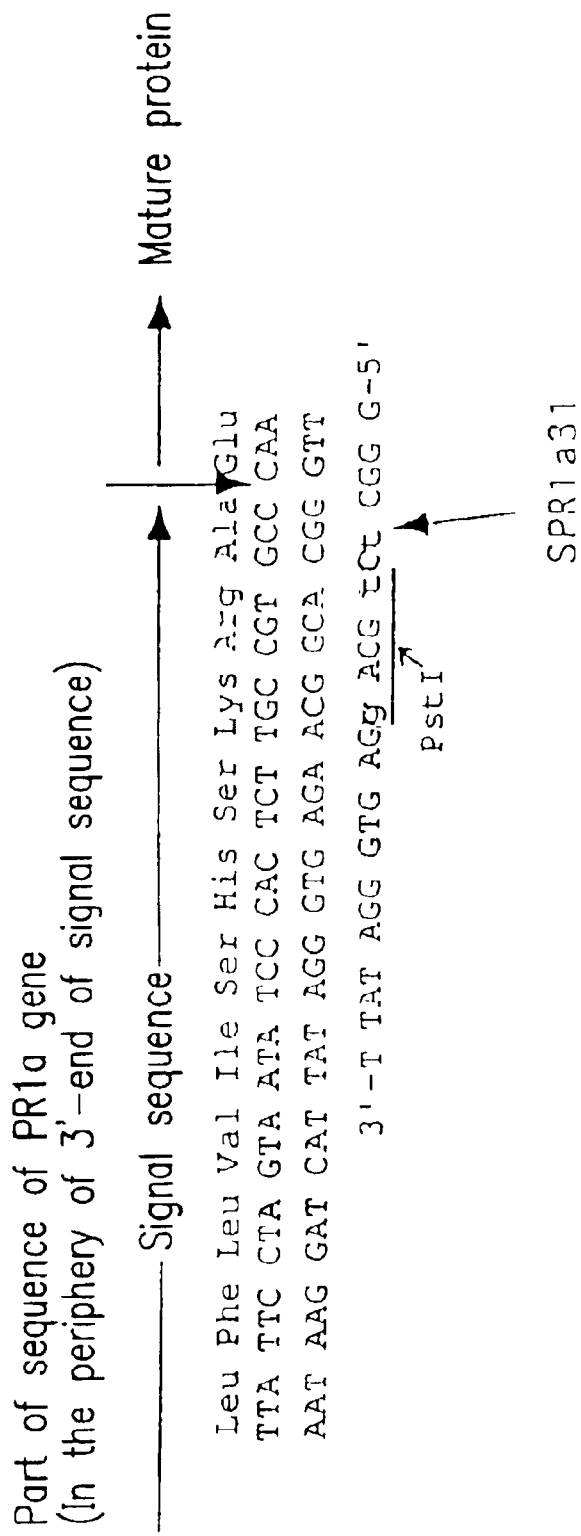
Figure 6:
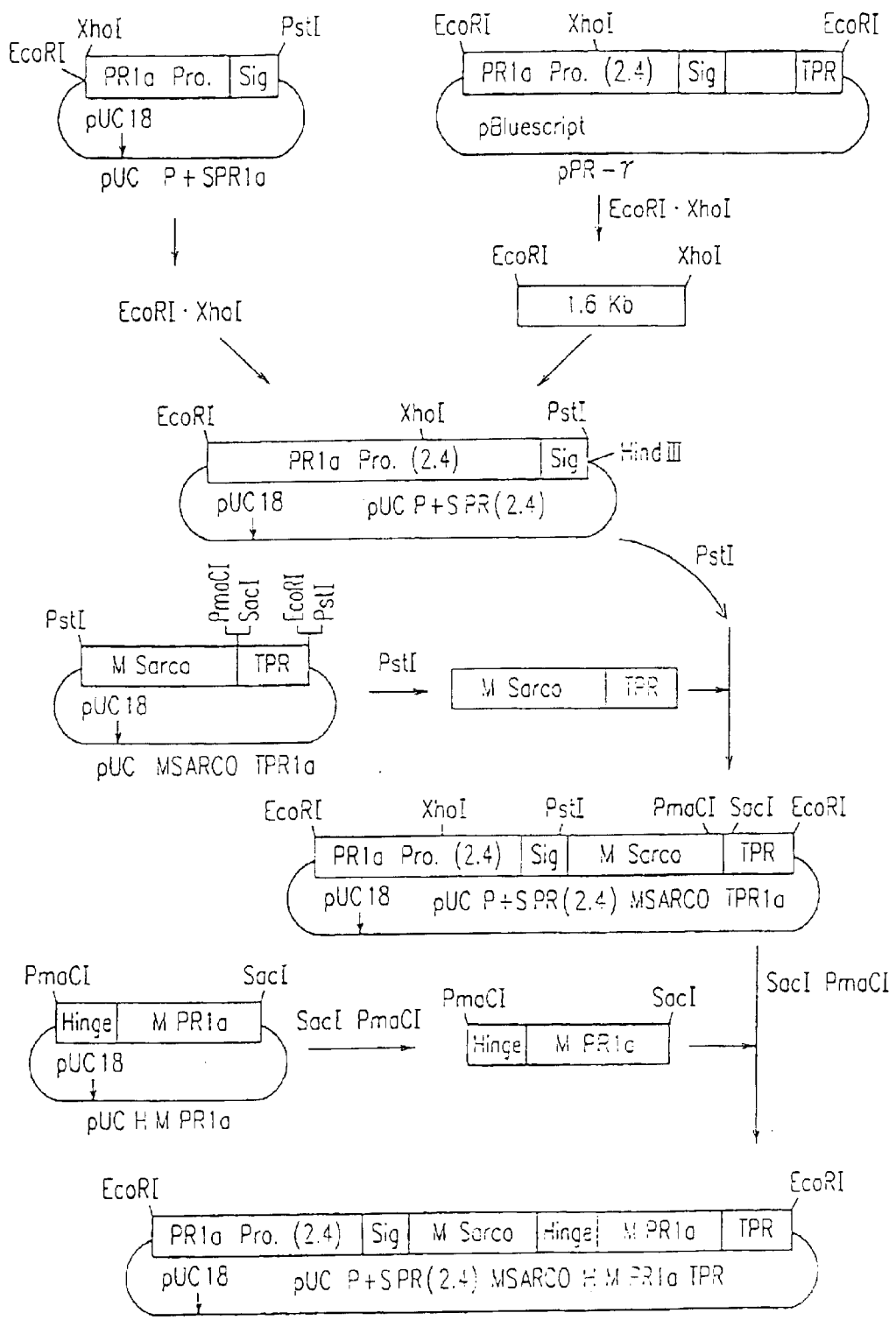
Figure 7:
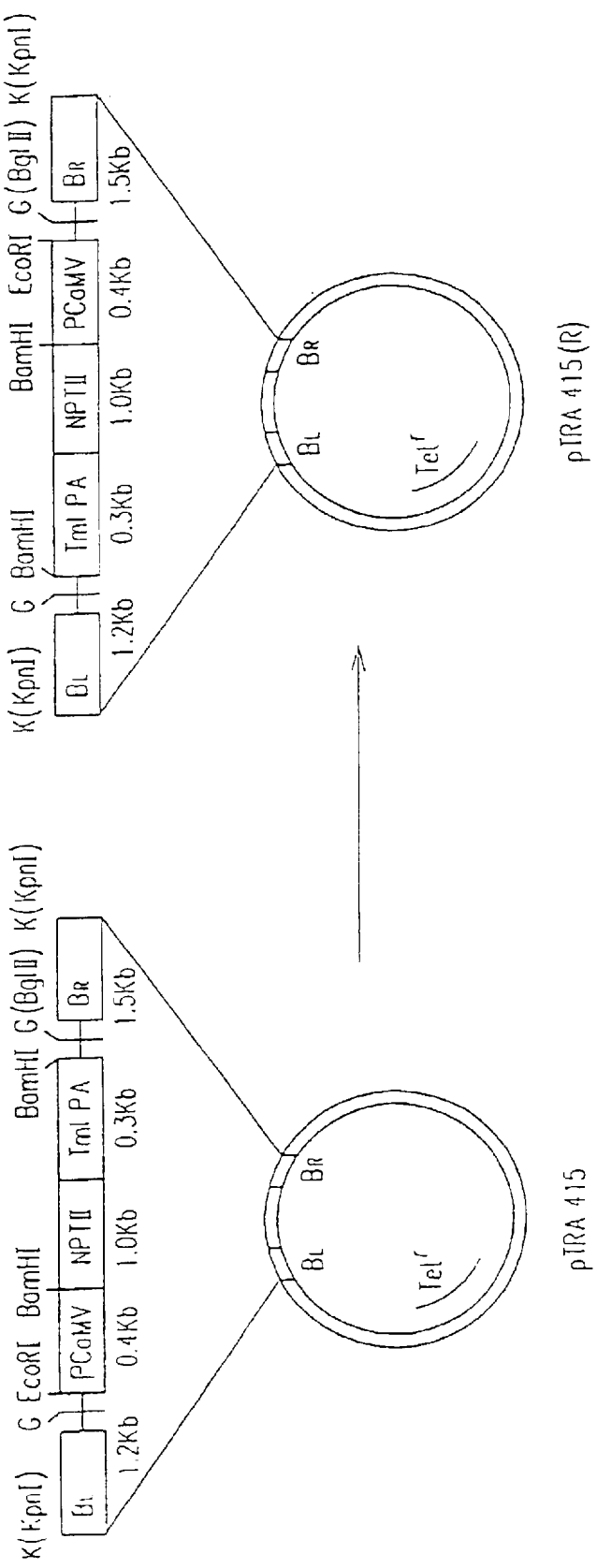
Figure 8:
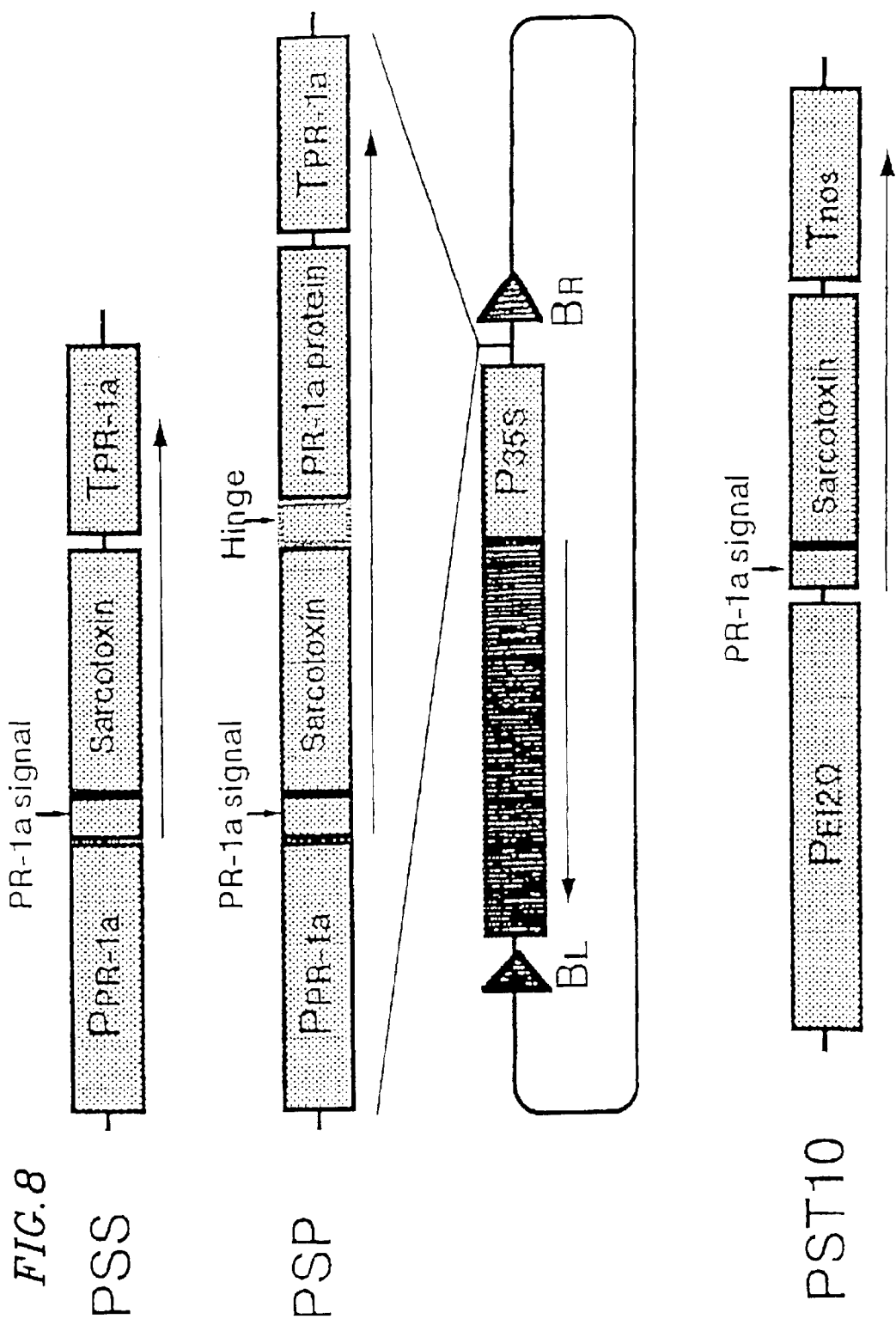
Figure 9:
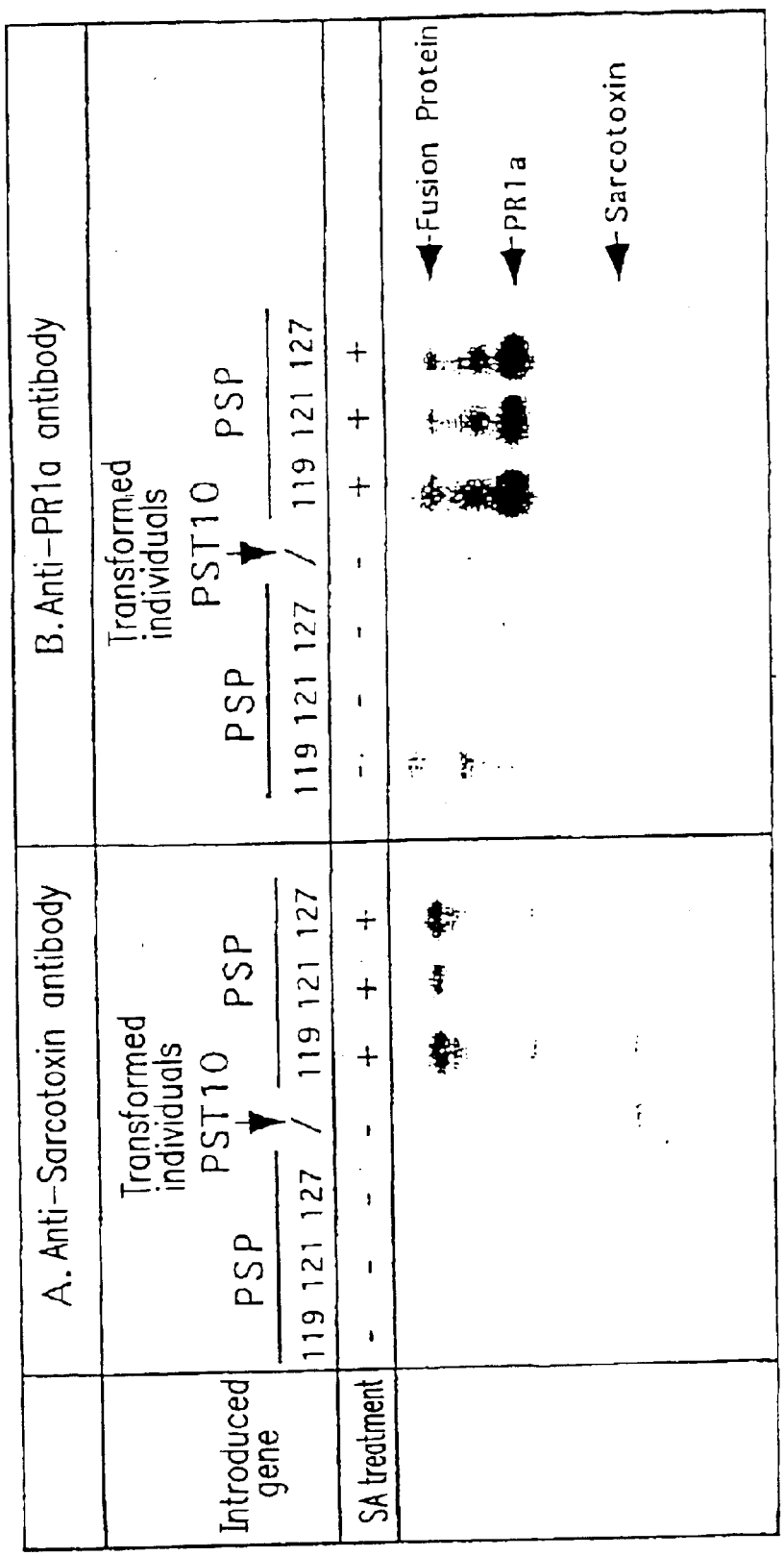
Figure 10:
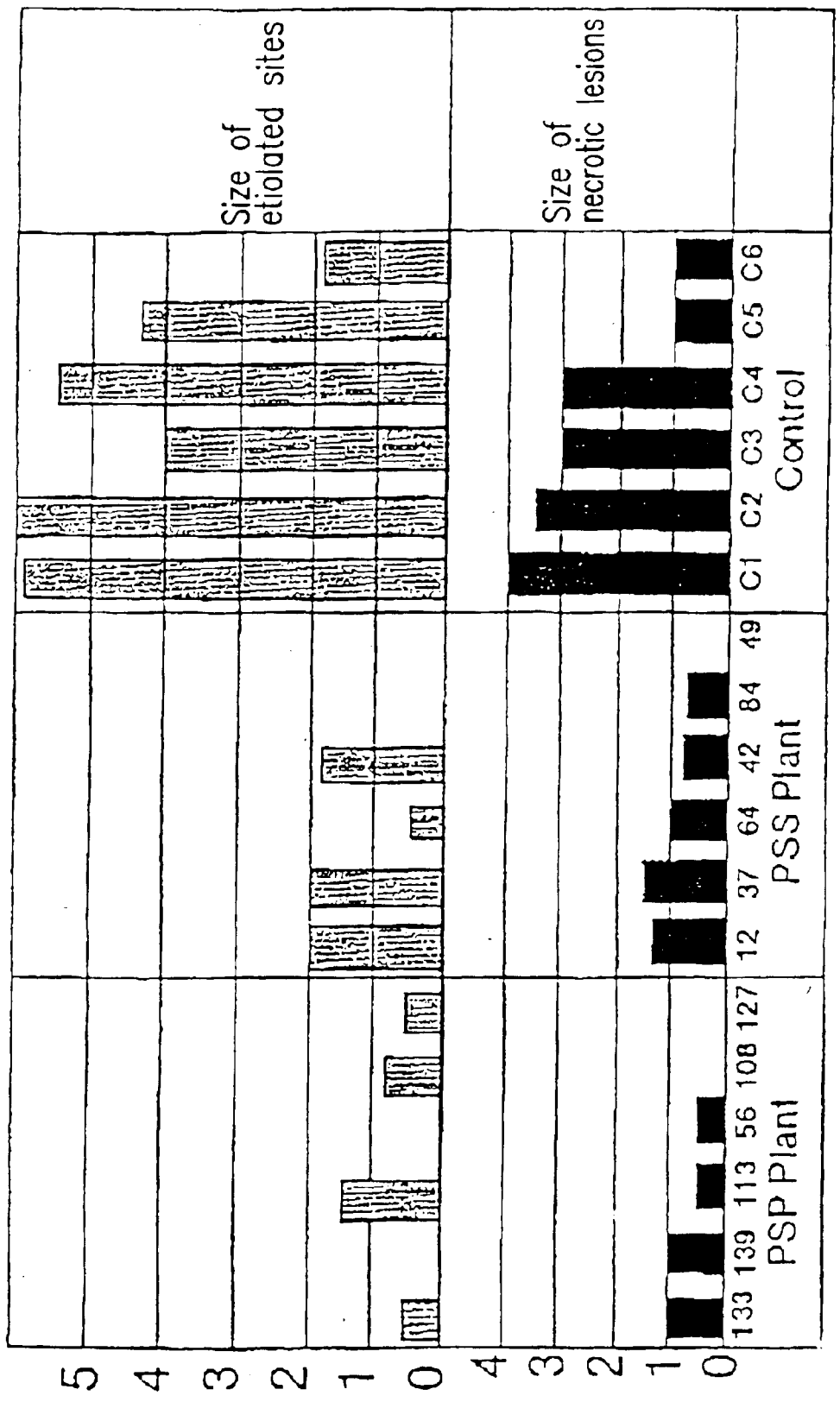
Figure 11:
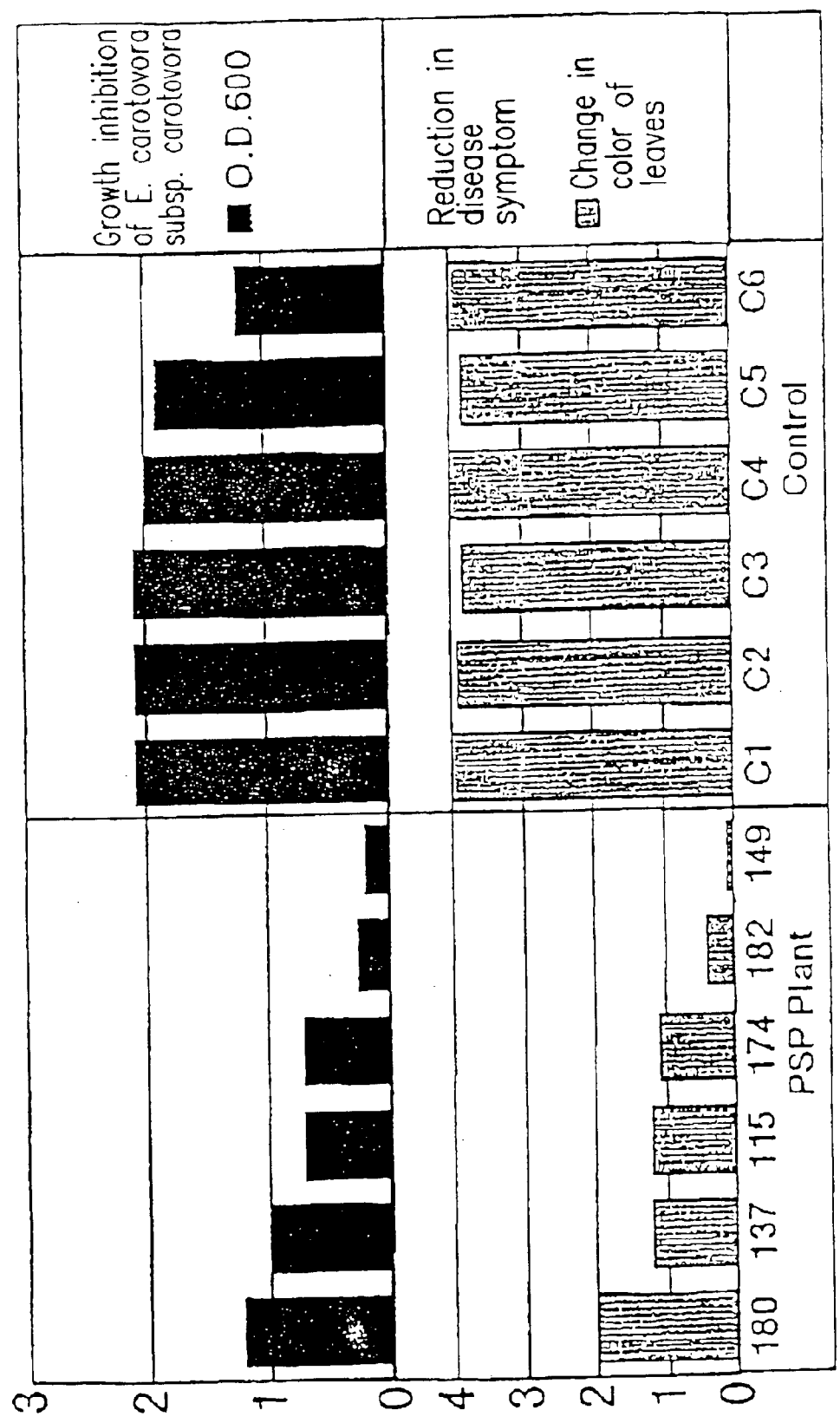

Using the plasmid pPR-γ having a genomic clone of the tobacco PR-1a gene shown in FIG. 1 as a template, a DNA fragment (TPR-1a fragment) having a terminator region of the PR-1a gene was obtained. The TPR-1a fragment was obtained by amplifying the terminator region of the PR-1a gene by PCR, using primers TPR-1a51 (SEQ ID NO. 3) and BKSBE (SEQ ID NO. 4). The TPR-1a51 has a sequence homologous to the 3' end of cDNA for Sarcotoxin 1a on a 5' end and further has a recognition sequence of SacI immediately downstream its stop codon. Also, a base is partially substituted immediately upstream the stop codon, as shown in FIG. 3. By this substitution of the base, a restriction enzyme PmaCI recognition site is newly introduced; however, there is no change in the amino acid sequence of Sarcotoxin 1a. On the other hand, the primer BKSBE has a sequence homologous to a sequence from an EcoRI site to a BamHI site of a vector portion of pPR-γ. This sequence is adjacent to a 3' end of a portion corresponding to the terminator of the PR-1a gene of the pPR-γ.

(3) Preparation of an HMPR-1a Fragment (a DNA Fragment Having a Hinge Region of the Tobacco Chitinase and a Region Encoding the Mature PR-1a Protein)

Using the plasmid pPR-γ having a genomic clone of the tobacco PR-1a gene shown in FIG. 1 as a template, a DNA fragment (HMPR-1a fragment) having a region encoding the mature PR-1a protein was obtained. The HMPR-1a fragment was obtained by amplifying a region of the PR-1a gene encoding a mature protein by PCR, using primers HMPR-1a51 (SEQ ID NO. 5) and MPR-1a31 (SEQ ID NO. 6). The 5' end of HMPR-1a51 has a sequence identical to a PmaCI site and a 12-base sequence adjacent to the PmaCI site of TPR-1a51. Furthermore, the primer HMPR-1a51 has a sequence identical to a region encoding a hinge region of tobacco chitinase at its 3' end.

Furthermore, the primer MPR-1a31 has a recognition site of a restriction enzyme SacI added thereto immediately downstream the stop codon at the 3' end.

(4) Preparation of an MSARCO Fragment (a DNA Fragment Having a Region Encoding a Mature Peptide of Sarcotoxin)

Using a known plasmid pTO19 (N. Matsumoto et al., BioChem. J., 239, 717 (1986)) containing cDNA of Sarcotoxin 1a as a template, a DNA fragment (MSARCO fragment) having a region encoding a mature peptide of Sarcotoxin was obtained. The MSARCO fragment was obtained by amplifying a region encoding the mature peptide of Sarcotoxin by PCR using primers MSARCO51 (SEQ ID NO. 7) and MSARCO31 (SEQ ID NO. 8). The sequences of the primers MSARCO51 and MSARCO31 are shown in FIGS. 4 and 5, respectively. The primer MSARCO51 has a sequence at 5' end homologous to a PstI site of SPR-1a31 and a 14-base sequence adjacent to the PstI site. In the MSARCO31, the recognition site of the restriction enzymes PmaCI and SacI are introduced adjacent to a sequence complementary to a region encoding a stop codon, as shown in FIG. 5. The restriction enzyme site was introduced in the same manner as TPR-1a51.

(5) Preparation of an MSARCO-TPR Fragment (a DNA Fragment in Which the MSARCO Fragment is Linked to the TPR-1a Fragment)

The MSARCO DNA fragment obtained in the above process (4) and the TPR-1a fragment obtained in the above process (2) were amplified by a recombinant PCR method using the primers MSARCO31 and BKSBE, thereby obtaining an MSARCO-TPR fragment.

(6) Preparation of a Recombinant Gene (Connection of a P+S PR-1a Fragment, an HMPR-1a Fragment, and an MSARCO-TPR-1a Fragment)

The P+S PR-1a fragment obtained in the above process (1), the HMPR-1a fragment obtained in the above process (3), and the MSARCO-TPR-1a fragment obtained in the above process (5) were cloned into plasmids pUC18, respectively. Each of the plasmids was named pUC P+S PR-1a, pUC H MPR-1a, and pUC MSARCO-TPR-1a (see FIG. 6). It was confirmed by using a sequencing kit and a sequence analyzing apparatus (Applied Biosystem) that sequences of interest were correctly inserted into these plasmids. DNA which was cloned into the plasmid pUC18 and in which a sequence was confirmed to be correct was used as a material for gene recombination. SEQ ID NO: 9 shows the sequence of a terminator portion of PR-1a which has been sequenced.

Hereinafter, the preparation of the recombinant gene of the present invention will be described with reference to FIG. 6.

First, a portion upstream (on the side of the 5' end) of an XhoI site in the PR-1a promoter region in the pPR-γ was digested with EcoRI and XhoI restriction enzymes. The resultant fragment of about 1.6 kb was purified with the Gene Clean Kit manufactured by Biol01. The above purified fragment of about 1.6 kb was inserted into the plasmid pUC P+S PR-1a having the P+S PR-1a fragment, which was previously digested with EcoRI and XhoI restriction enzymes. The resulting plasmid (pUC P+C PR(2.4)) contains the full-length PR-1a promoter and a DNA region encoding the PR-1a signal sequence as inserts. This plasmid has a cassette of the tobacco PR-1a promoter which may be removed by digestion with an EcoRI restriction enzyme.

The pUC MSARCO-TPR-1a was digested with a PstI restriction enzyme, and the DNA fragment corresponding to the MSARCO-TPR-1a was purified. This DNA fragment was inserted into a PstI site of pUC P+S PR(2.4). Among the plasmids thus obtained, a plasmid (pUC P+S PR(2.4) MSARCO-TPR-1a) in which the DNA fragment was correctly inserted in the direction of P+S PR-1a-MSARCO-TPR-1a was selected. The plasmid has a cassette (cassette PSS) of a gene encoding a non-fusion expressible Sarcotoxin, controlled by the tobacco PR-1a promoter. This cassette may be removed by digestion with EcoRI.

Then, an H MPR-1a portion was isolated from the plasmid pUC H MPR-1a using PmaCI and SacI restriction enzymes. On the other hand, the pUC P+S PR(2.4) MSARCO-TPR-1a was digested with PmaCI and SacI restriction enzymes, and the H MPR-1a portion was inserted into this site (pUC P+S PR-1a(2.4) MSARCO H MPR-1a TPR). The plasmid has a recombinant gene in which a foreign gene, i.e., the gene for the Sarcotoxin 1a, which is an anti-bacterial peptide derived from a Diptera insect, is linked to a plant gene, i.e., the tobacco PR-1a gene via a hinge region of tobacco chitinase. Furthermore, the plasmid has a recombinant gene encoding a fusion protein Sarcotoxin 1a-PR-1a controlled by the tobacco PR-1a promoter. When digested with EcoRI, an expression cassette (cassette PSP) for expressing a recombinant gene of the invention may be removed. This cassette consists of P+S PR-1a(2.4) MSARCO H MPR-1a TPR, encoding an expressible fusion protein Sarcotoxin 1a-hinge-PR-1a under the control of the tobacco PR-1a promoter.

EXAMPLE 2

Construction of an Expression Vector

A binary vector pTRA415 (FIG. 7) (Ohshima et al., Plant Cell, vol. 2, pp. 95–106 (1990)) has a sequence in which the NPT gene is inserted within a BglII—BglII fragment downstream of the CaMV 35S promoter. The pTRA415 was digested with BglII, ligated with ligase, and then introduced into *E. coli* JM109. A plasmid (pTRA415-(R)) was selected among transformants, in which the BglII—BglII fragment of the pTRA415 was inserted in an opposite direction. The plasmid pTRA415(R) has the NPT gene controlled by the CaMV 35S promoter as a marker gene in a T-region and has a unique EcoRI site on the right side of the NPT gene. When a foreign gene is introduced into this EcoRI site, the marker gene is mobilized after the foreign gene is mobilized in a plant.

The plasmid pUC P+S PR-1a(2.4) MSARCO TPR (plasmid expressing a non-fusion Sarcotoxin) was digested with EcoRI to remove the cassette PSS. The cassette PSS was inserted into the EcoRI site of the plasmid pTRA415 (R). A plasmid PSS was selected from the resulting plasmids, in which the PR-1a promoter of the inserted expression cassette was inserted so as to be next to the CaMV 35S promoter of the marker gene.

Similarly, the plasmid pUC P+S PR-1a(2.4) MSARCO H MPR-1a TPR (plasmid expressing a fusion Sarcotoxin-PR-1a protein) was digested with EcoRI to remove a cassette PSP. The cassette PSP was inserted into the EcoRI site of the plasmid pTRA415(R). A plasmid PSP was selected from the resulting plasmids, in which the PR-1a promoter of the inserted expression cassette was inserted so as to be next to the CaMV 35S promoter of the marker gene.

EXAMPLE 3

Introduction of an Expression Vector into Tobacco (1) Transformation of *Agrobacterium tumefaciens*

*Agrobacterium tumefaciens* was cultured in a medium containing 250 μg/ml of streptomycin and 50 μg/ml of rifampicin at 28° C. A culture medium was prepared in accordance with a method of Nagel et al. (Micribiol. Lett., 67, 325 (1990)). An expression vector (plasmid PSP) was introduced into the *Agrobacterium tumefaciens* by electroporation. Similarly, the plasmid PSS (vector for expressing the non-fusion Sarcotoxin) and the plasmid PST10 described in Japanese Laid-Open Patent Publication No. 7-250685 were introduced into the *Agrobacterium tumefa-*

*ciens* by electroporation (This is the vector for constitutively expressing a non-fusion Sarcotoxin). Each of the plasmids PSP, PSS, and PST 10 used in the present invention is schematically shown in FIG. 8.

(2) Transformation of Tobacco

Agrobacterium transformed with the plasmid PSP by the above method was obtained and suspension culture in a YEB medium (DNA cloning, vol. 2, p. 78). The culture medium was then 20-fold diluted with sterilized water and then cocultivated with leaf disks of tobacco (*Nicotiana tabacum* Samsun NN). After a few days, this mixture was transferred to a medium containing antibiotics so as to remove the Agrobacterium. The leaf disks were subcultured in a selection medium once every two weeks. Transformed tobacco cells were selected and regenerated by the conventional methods to obtain 29 independent transformants.

Similarly, transformants transformed with the plasmid PSS or the plasmid PST10 were obtained.

EXAMPLE 4

Detection of a Fusion Protein in a Transgenic Plant by Western Blotting

Soluble protein extracts were prepared from a plant transformed with the plasmid PSP, a plant transformed with the plasmid PST10, and a wild-type Samsun NN plant, respectively, in the following manner. Four leaf disks with a diameter of about 7 mm were punched off from the tobacco leaves, respectively. Two leaf disks from each tobacco leaf were floated on an aqueous solution of 0.5 mM salicylic acid and the other two leaf disks thereof were floated on distilled water as controls. The leaf disks were cultured for two days under this condition. Thereafter, these leaf disks were homogenized in 20 $\mu l$ of 50 mM Na—$PO_4$ (pH 7.0), 1 mM Na-EDTA, 10 $\mu M$ A-PMSF, 0.5 $\mu g/ml$ Leupeptin, and 2 mM DTT and centrifuged at 10,000 rpm for 10 minutes, respectively, and supernatants were collected as protein extracts. Then, 2.5 $\mu l$ each of the protein extracts was separated by SDS-PAGE as described in Analytical Biochemistry 166, 368–379 and transferred to a PVDF membrane. Thereafter, bands which reacted with anti-Sarcotoxin antibodies were immunologically detected. The result of the western blotting is shown in FIG. 9.

In the transgenic plant (PSP plant) obtained by transformation with the plasmid PSP, a band which was considered to be the fusion protein was detected irrespective of whether or not a treatment with salicylic acid was carried out. However, the amount of the detected fusion protein remarkably increased by the induction of salicylic acid. Furthermore, by the treatment with salicylic acid, a band which was considered to be a free (non-fusion) Sarcotoxin appeared. A band which was considered to be Sarcotoxin was detected in the PST10 plant, and the band which has same mobility was also detected in the PSP plant. A band reacting with the anti-Sarcotoxin antibodies was not detected in the Samsun NN plant. The similar experiment was carried out, except for using anti-PR-1a antibodies in place of the anti-Sarcotoxin antibodies. As a result, the band which has low mobility seen in the PSP plant were considered to be recognized even using the anti-PR-1a antibodies. Thus, the band which has low mobility was considered to be a fusion protein.

EXAMPLE 5

Resistance Against *P. syringae* pv. *tabaci* Infection in PSP Plants

Transgenic tobacco leaves and control tobacco leaves were scratched at four portions by using a needle and were inoculated with a suspension of $2\times10^7$ ml of *P. syringae* pv. *tabaci*. The similar treatment was carried out four times with respect to each plant. After six days, the degree of disease symptom was determined based on the size of necrotic lesions and the changes in color of the leaves.

The necrotic lesions were evaluated by using the following numerical values.

0 No necrotic sites are recognized.

1 The diameter of a necrotic site is 3 mm or less.

2 The diameter of a necrotic site is 5 mm or less.

3 The diameter of a necrotic site is 10 mm or less.

4 The diameter of a necrotic site is 10 mm or more.

The etiolated sites were evaluated by using the following numerical values.

0 No etiolated sites are recognized.

1 Light etiolated sites with a diameter of about 5 mm are recognized.

2 Etiolated sites with a diameter exceeding 5 mm are recognized.

3 Etiolated sites with a diameter of 10 mm or more are recognized.

4 Necrotic sites are enlarged with the etiolation of the inoculated sites.

The result is shown in FIG. 10. In some transgenic tobacco with the fusion gene, the disease symptom caused by *P. syringae* pv. *tabaci* was recognized to be reduced, compared with that in the control plants.

It is understood that the resistance increased more when using the expression cassette of the present invention than in the case of expressing Sarcotoxin above.

EXAMPLE 6

Resistance Against *E. carotovora* subsp. *carotovora* Infection in PSP Plants Four leaf disks with a diameter of 7 mm were punched off from transformed tobacco leaves and control tobacco leaves, respectively. Two leaf disks were floated on a suspension of $4\times10^7$ ml of *E. carotovora* subsp. *carotovora* and the other two leaf disks were floated on distilled water as control. After three days, the degree of the disease symptom and the growth of the bacteria were determined based on the changes in color of the leaves and the changes in turbidity of the suspension, respectively. The results are shown in FIG. 11.

In some transgenic tobacco with the fusion gene of this invention, the degree of disease symptom caused by *E. carotovora* subsp. *carotovora* was reduced, compared with the control tobacco. Simultaneously, the growth of *E. carotovora* subsp. *carotovora* was suppressed.

It was made clear from the above results that the introduction of the gene encoding the fusion protein allows a plant which confers resistance to *P. syringae* pv. *tabaci* and *E. carotovora* subsp. *carotovora* to be obtained.

EXAMPLE 7

Measurement of an Anti-Fungal Activity of Sarcotoxin 1a in Vitro

Sarcotoxin 1a was measured for an anti-fungal activity against *Fusarium oxysporum* F-3, *Rhizoctonia solani*, and *Rhizoctonia solani* AG-4 1272.

It has not been known if Sarcotoxin 1a has an anti-fungal activity and how to measure the activity. Therefore, a pre-culture medium and a test medium were variously studied. The pre-culture medium, in which a lawn may be uniformly enlarged within a short period of time, was selected. The test medium, which controls the extension of hyphae as much as possible and allows easy confirmation, was selected.

(1) Preparation of a Plate for Detection

The following three kinds of test media were prepared.

(i) Czapek's modified medium (10 g of sucrose, 0.5 g of $MgSO_4 \cdot 7H_2O$, 2.0 g of $NaNO_3$, 0.01 g of $Fe_2(SO_4)_3$, 1.0 g of $K_2HPO_4$, 0.5 g of KCl, 15 g of agarose per liter, pH 6.8 to 7.0; used for *Rhizoctonia solani* AG-4 1272), (ii) 5-fold diluted PDA medium (7.8 g of Bacto (Trademark) Poteto Dextrose Agar, 12 g of agarose per liter; used for *Fusarium oxysporum* F-3), (iii) $Na_2HPO_4$—$NaH_2PO_4$ buffer (15 g/l agarose, pH 5.8; used for *Rhizoctonia solani*).

Figure 12:
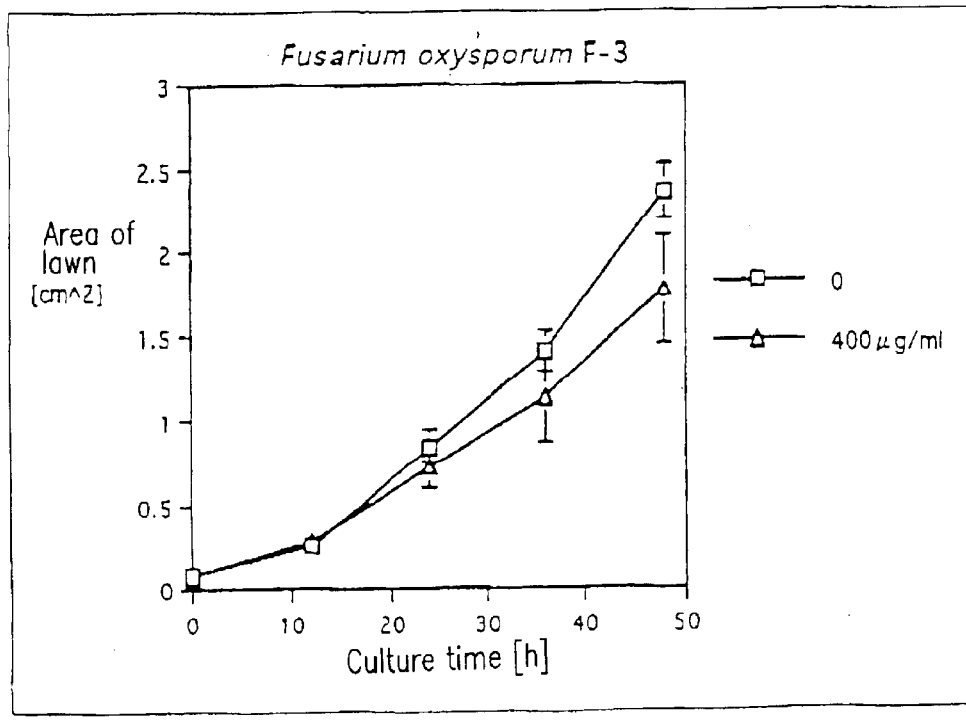
Figure 13:
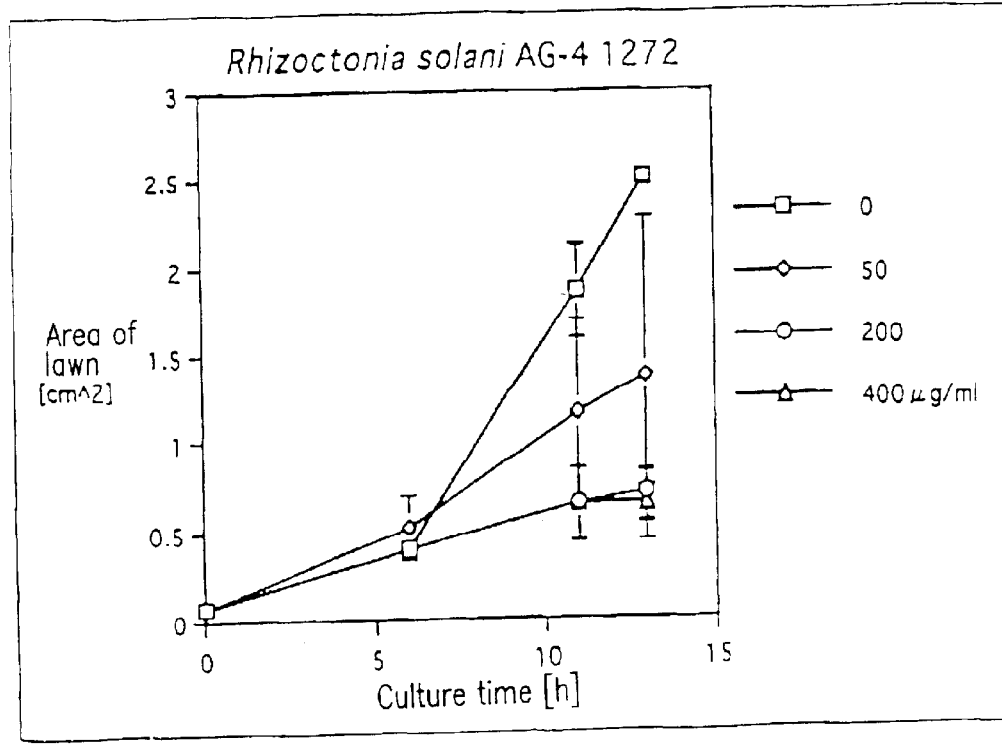
Figure 14:
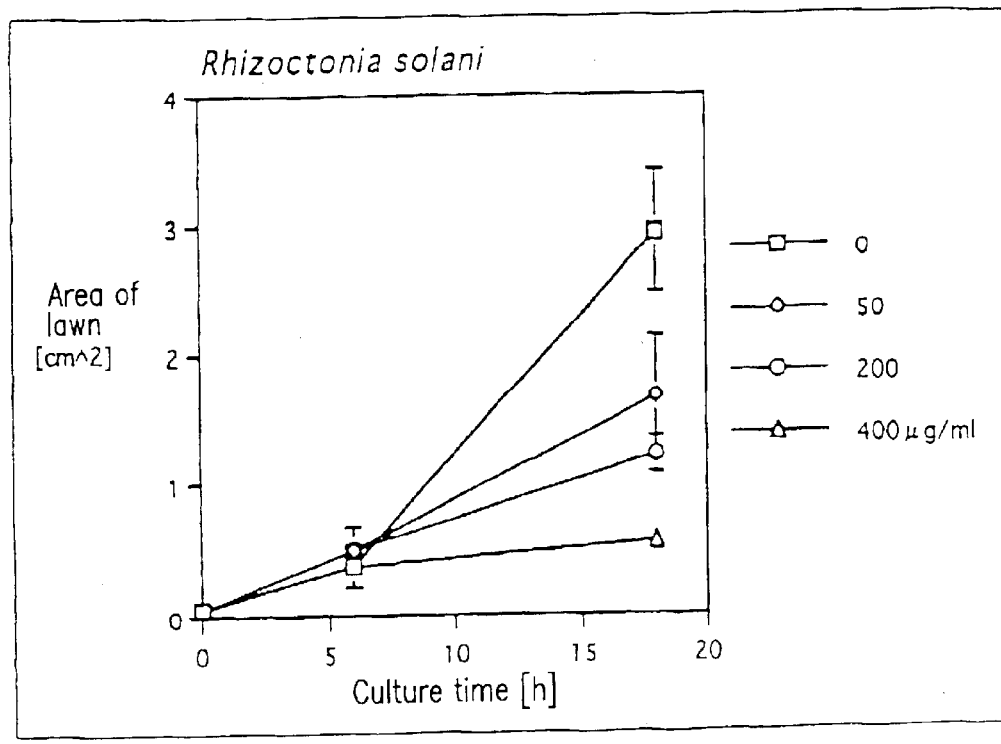

The media for detection were autoclaved. When the media was cooled to 50° C., Sarcotoxin 1a (synthesized by a peptide synthesis and purified to 99% or more by HPLC) was added to each medium. Each of the resulting media was dispensed into a 12-well microplate at 400 μl per well and solidified. The final concentration of Sarcotoxin 1a is as shown in FIGS. 12 to 14.

(2) Inoculation of Pathogenic Fungi (a) Pre-culture

*Fusarium oxysporum* F-3, *Rhizoctonia solani*, and *Rhizoctonia solani* AG-4 1272 were respectively pre-cultured in a PDA media (39 g/l Bacto (Trademark) Poteto Dextrose Agar) at 22° C. for 2 days.

(b) Inoculation of Pathogenic Fungi

An outermost lawn of each hypha spreading over almost the entire surface of the PDA medium of a 9 cm-petri dish was punched with a cork borer with a diameter of 4 mm, and each fungi was placed in the center of a well of a test plate in such a manner that the surface of the layer faced down. Each test plate for detection was kept at 22° C. in the dark.

(c) Assay of Anti-Fungal Activity of Sarcotoxin 1a

Each test plate inoculated with the above-mentioned pathogenic fungi was measured for the size of each hypha growing under transmitted light at established periods, and the area of each hypha and a standard deviation were calculated (see FIGS. 12, 13, and 14). As shown in these figures, anti-fungal properties of Sarcotoxin 1a showed a concentration-dependent manner. Thus, Sarcotoxin 1a was assumed to be effective for fungi.

EXAMPLE 8

Resistance Against *Rhizoctonia solani* Infection in Transgenic Tobacco

Transgenic tobacco with the fusion genes (PSS or PSP) and tobacco obtained by transformation with 35S-GUS as a control were self-pollinated. The resulting seeds were plated over media containing 50 μg/ml of kanamycin, and about 8 mm-long young plants were obtained after 20 days. Then, 30 young plants of the transgenic tobacco and those of the control were uniformly planted respectively on petri dishes having a diameter of 9 cm containing sugar-free MS agar medium (see T. Murashige and F. Skoog, (1962), A reversed medium of rapid growth and bioassays with tobacco tissue cultures, Physiologia Plantarum, vol. 15, pp. 473–497) and allowed to stand for 3 days. Then, the lawn obtained by pre-culturing *Rhizoctonia solani* was cut into 3 mm-chips, and 7 chips were uniformly placed on agar per petri dish, whereby these young plants were inoculated with the *Rhizoctonia solani*. Each petri dish was kept at 22° C. On the sixth day after inoculation, green surviving individuals were identified as resistant plants. The result is shown in Table 1.

TABLE 1

Resistance against *Rhizoctonia solani* infection detected in transgenic tobacco

| Plant | Number of surviving plants (Number of healthy plants) |
| --- | --- |
| Control (35S-GUS) | 2 (0) |
| PSS12 | 1 (1) |
| PSS41 | 8 (7) |
| PSS42 | 1 (1) |
| PSP115 2 | 4 (2) |
| PSP121 | 2 (0) |
| PSP137 | 2 (0) |

The PSP and PSS transgenic plants showed resistance to *Rhizoctonia solani*. In the table, the numerical values in brackets show the number of green resistant individuals, particularly, the number of individuals growing vigorously.

EXAMPLE 9

Resistance Against *Pythium aphanidermatum* Infection in Transgenic Tobacco

Transgenic tobacco with the fusion genes (PSS or PSP) and tobacco obtained by transformation with 35S-GUS as a control were self-pollinated. The resulting seeds were plated over media containing 50 μg/ml of kanamycin, and about 8 mm-long young plants were obtained after 20 days. Then, 30 young plants of the transgenic tobacco and those of the control were uniformly planted respectively on petri dishes having a diameter of 9 cm containing an sugar-free MS agar medium and allowed to stand for 1 day. Then, the lawn obtained by pre-culturing *Pythium aphanidermatum* was cut into 3 mm-chips, and 7 chips were uniformly placed on agar per petri dish, whereby these young plants were inoculated with the *Pythium aphanidermatum* bacterium. Each petri dish was kept at 22° C. On the 14th day after inoculation, green surviving individuals were identified as resistant plants. The result is shown in Table 2.

TABLE 2

Resistance against *Pythium aphanidermatum* infection detected in the transgenic tobacco

| Plant | Number of surviving plants (number of healthy plants) |
| --- | --- |
| Control (35S-GUS) | 9 (0) |
| PSS12 | 6 (3) |
| PSS41 | 23 (15) |
| PSS42 | 12 (1) |
| PSP115 | 9 (1) |
| PSP121 | 9 (0) |
| PSP137 | 7 (0) |

The PSP and PSS transgenic plants showed resistance to *Pythium aphanidermatum*. In the table, the numerical values in brackets show the number of green resistant individuals, particularly, the number of individuals growing vigorously.

EXAMPLE 10

Resistance against *Phytophthora infestans* Infection in the Transgenic Tobacco The surfaces of the leaves of a transgenic plant and a control tobacco plant were respectively rubbed with the back of a small spatula (in the form of a stainless steel plate with a width of 6 mm) so as to be scratched at 6 portions. A flat medium in which the lawn of a pre-cultured *Phytophthora infestans* spread was cut into chips with a size of about 3 mm. The chips were placed on the scratched sites rubbed with the back of a small spatula, whereby the leaves were inoculated with the *Phytophthora infestans*. After a predetermined period of time, the degree of the disease symptom (the size of brown lesions) in the inoculated sites was investigated. The total size of the brown lesions at 6 portions was used as an index of the disease symptom of each plant.

The lesions were evaluated using the following numerical values.

0 No lesions are found.
1 Brown lesions with a diameter of 5 mm or less are found.
2 Brown lesions with a diameter of 5 mm to 10 mm are found.
3 Brown lesions with a diameter of 10 mm to 20 mm are found.
4 Brown lesions with a diameter of 20 mm or more are found.

Figure 15:
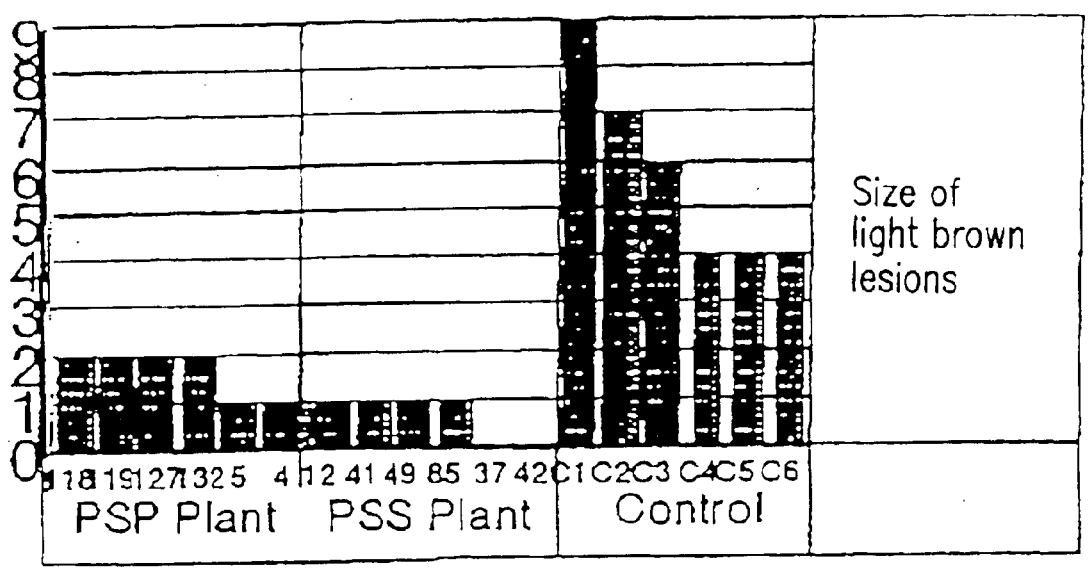

The results of 6 individuals of the transgenic tobacco which showed high resistance and the control tobacco are shown in FIG. 15. Among the transgenic plants, those which showed high resistance to infection caused by *Phytophthora infestans* were obtained. In particular, 2 individuals which showed no disease symptoms were found in the PSS transgenic plant.

Thus, these plants of the present invention, which transformed with a gene encoding for antibacterial peptide, show resistance to bacterial and fungal pathogens.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

---

What is claimed is:

1. A method of conferring resistance to pathogenic fungi on a plant, wherein the method comprises the steps of:

transforming a plant cell with an expression vector, wherein said expression vector comprises:
an expression cassette comprising a first plant promoter induced by stress operably linked to a DNA sequence encoding Sarcotoxin 1a, wherein a DNA sequence encoding a signal peptide is operatively positioned between the first plant promoter and the DNA sequence encoding Sarcotoxin 1a; and a constitutively expressed plant promoter positioned adjacent to the first plant promoter; and regenerating the plant cell into a transgenic plant, wherein the transgenic plant has enhanced resistance to pathogenic fungi as compared to a corresponding untransformed plant.

2. The method according to claim 1, wherein said expression vector further comprises a drug resistance gene operably linked to the constitutively expressed plant promoter.

3. The method according to claim 1, wherein a DNA sequence encoding a plant protein is operatively fused to the DNA sequence encoding Sarcotoxin 1a via the hinge region of the tobacco chitinase gene.

4. The method according to claim 1, wherein the DNA sequence encoding the signal peptide is from a plant gene.

5. The method according to claim 1, wherein the promoter induced by stress is the promoter of a tobacco PR-1a gene.

6. The method according to claim 2, wherein the expression cassette further comprises the terminator of the tobacco PR-1a gene operably linked downstream of the DNA sequence encoding Sarcotoxin 1a.

7. The method according to claim 1, wherein the constitutively expressed plant promoter is a cauliflower mosaic virus 35S promoter.

8. The method according to claim 1, wherein the signal peptide is the PR-1a signal peptide.

9. A transgenic plant which is resistant to pathogenic fungi, wherein the plant comprises an expression vector, wherein the expression vector comprises:
- a first expression cassette comprising a DNA sequence encoding Sarcotoxin 1a operably linked to a promoter induced by stress, wherein a DNA sequence encoding a signal peptide is operatively positioned between the promoter induced by stress and the DNA sequence encoding Sarcotoxin 1a; and
- a second expression cassette comprising a drug resistance gene operably linked to a constitutively expressed promoter;
- wherein the first and second expression cassettes are positioned adjacent to each other, and wherein the transgenic plant has enhanced resistance to pathogenic fungi as compared to a corresponding untransformed plant.

10. The plant according to claim 9, wherein a DNA sequence encoding a plant protein is operatively fused to the DNA sequence encoding Sarcotoxin 1a via the hinge region of the tobacco chitinase gene.

11. The plant according to claim 9, wherein the DNA sequence encoding the signal peptide is from a plant gene.

12. The plant according to claim 9, wherein the promoter induced by stress is a promoter of the tobacco PR-1a gene.

13. The plant according to claim 9, wherein the first expression cassette further comprises the terminator of the tobacco PR-1a gene operably linked downstream of the DNA sequence encoding Sarcotoxin 1a.

14. The plant according to claim 9, wherein the constitutively expressed promoter is a cauliflower mosaic virus 35 S promoter.

15. The plant according to claim 9, wherein the expression vector further comprises a T-DNA region.

16. The plant according to claim 9, wherein the signal peptide is the PR-1a signal peptide.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..32
      (D) OTHER INFORMATION: /note= "PR-1a51 primer"

(xi) SEQUENCE DESCRIPTION: SEQ ID NO:1:

AGTAGAATTC TTAAAACACC CTCGAGGATT TC      32

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..23
      (D) OTHER INFORMATION: /note= "SPR-1a31 primer"

(xi) SEQUENCE DESCRIPTION: SEQ ID NO:2:

GGGCTCTGCA GGAGTGGGAT ATT      23

(2) INFORMATION FOR SEQ ID NO:3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..43
        (D) OTHER INFORMATION: /note= "TPR-1a51 primer"

(xi) SEQUENCE DESCRIPTION: SEQ ID NO:3:

ACAGCACGTG GTTAATTGAG CTCGAAACGA CCTACGTCCA TTC         43

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "BKSBE primer"

(xi) SEQUENCE DESCRIPTION: SEQ ID NO:4:

TCCCCCGGGC TGCAGGAATT C         21

(2) INFORMATION FOR SEQ ID NO:5:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..72
        (D) OTHER INFORMATION: /note= "HMPR-1a51 primer"

(xi) SEQUENCE DESCRIPTION: SEQ ID NO:5:

TACACACGTG GTCCCACACC TACACCCCCC ACCCCACCCG GTGGTGGGCA AAATTCTCAA    60

CAAGACTATT TG         72

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..30
        (D) OTHER INFORMATION: /note= "MPR-1a31 primer"

(xi) SEQUENCE DESCRIPTION: SEQ ID NO:6:

TATCGAGCTC AATTAGTATG GACTTTCGCC         30

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "MSARCO51 primer"

(xi) SEQUENCE DESCRIPTION: SEQ ID NO:7:

```
CACTCCTGCA GAGCCGGTTG GTTGAAAAAG ATTGGC                                36
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "MSARCO31 primer"

(xi) SEQUENCE DESCRIPTION: SEQ ID NO:8:

```
TTTCGAGCTC AATTAACCAC GTGCTGTAGC AGC                                   33
```

(2) INFORMATION FOR SEQ ID NO:9:

(i) SEQUENCE CHARACTERISTICS:
        (A) LENGTH: 508 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..508
        (D) OTHER INFORMATION: /note= "tobacco PR-1a terminator"

(xi) SEQUENCE DESCRIPTION: SEQ ID NO:9:

```
TTGAAACGAC CTACGTCCAT TTCACGTTAA TATGTATGGA TTGTTCTGCT TGATATCAAG       60

AACTTAAATA ATTGCTCTAA AAAGCAACTT AAAGTCAAGT ATATAGTAAT AGTACTATAT      120

TTGTAATCCT CTGAAGTGGA TCTATAAAAA GACCAAGTGG TCATAATTAA GGGGAAAAAT      180

ATGAGTTGAT GATCAGCTTG ATGTATGATC TGATATTATT ATGAACAGCG TTTTGTACTC      240

ATACGAATCA TGTGTTGATG GTCTAGCTAC TTGCGATATT ACGAGCAAAA TTCTTAACTA      300

CATGCCTTAG GAACAAGCTT ACACAGTTCA TATAATCTAC TAGAGGGCCA AAAACATGAA      360

AATTACCAAT TTAGATGGTA GGAGGATATT GAAAGTGGAG CAGCTAGTTT TAATAACTGA      420

CCGTTAGTCT TAAAATTGAC GGTATAAAAA TATTTACATA ATCAGGTCAT TTATAAGGTA      480

ATTATAGGTA AATATTTATG ACGAATTC                                        508
```

(2) INFORMATION FOR SEQ ID NO:10:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..36
            (D) OTHER INFORMATION: /note= "region of PR1a gene encoding
                3' end of signal sequence and start of
                mature protein"

(xi) SEQUENCE DESCRIPTION: SEQ ID NO:10:

TTATTCCTAG TAATATCCCA CTCTTGCCGT GCCCAA                                    36

(2) INFORMATION FOR SEQ ID NO:11:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Region
            (B) LOCATION: 1..12
            (D) OTHER INFORMATION: /note= "amino acid sequence of region
                of PR1a gene encoding 3' end of signal
                sequence and start of mature protein"

(xi) SEQUENCE DESCRIPTION: SEQ ID NO:11:

Leu Phe Leu Val Ile Ser His Ser Lys Arg Ala Glu
1               5                   10

(2) INFORMATION FOR SEQ ID NO:12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..27
            (D) OTHER INFORMATION: /note= "region of sarcotoxin gene
                encoding C-terminal of mature peptide"

(xi) SEQUENCE DESCRIPTION: SEQ ID NO:12:

GCTGCTACAG CCAGAGGTTA ATTGAAA                                              27

(2) INFORMATION FOR SEQ ID NO:13:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Region
            (B) LOCATION: 1..6
            (D) OTHER INFORMATION: /note= "C-terminal of mature sarcotoxin peptide"

(xi) SEQUENCE DESCRIPTION: SEQ ID NO:13:

Ala Ala Thr Ala Arg Gly
1               5

(2) INFORMATION FOR SEQ ID NO:14:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: -
       (B) LOCATION: 1..30
       (D) OTHER INFORMATION: /note= "region of PR1a gene encoding
           C-terminal of mature protein"

(xi) SEQUENCE DESCRIPTION: SEQ ID NO:14:

CCATACTAAT TGAAACGACC TACGTCCATT                                      30

(2) INFORMATION FOR SEQ ID NO:15:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: -
       (B) LOCATION: 1..45
       (D) OTHER INFORMATION: /note= "TPR1a51 from FIG. 3"

(xi) SEQUENCE DESCRIPTION: SEQ ID NO:15:

GCTGCTACAG CACGTGGTTA ATTGAGCTCG AAACGACCTA CGTCC                     45

(2) INFORMATION FOR SEQ ID NO:16:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: -
       (B) LOCATION: 1..27
       (D) OTHER INFORMATION: /note= "region of sarcotoxin gene
           encoding N-terminal of mature peptide"

(xi) SEQUENCE DESCRIPTION: SEQ ID NO:16:

GGTTGGTTGA AAAGATTGG CAAAAAA                                          27

(2) INFORMATION FOR SEQ ID NO:17:

(i) SEQUENCE CHARACTERISTICS:
       (A) LENGTH: 9 amino acids
       (B) TYPE: amino acid
       (C) STRANDEDNESS:
       (D) TOPOLOGY: linear (ii) MOLECULE TYPE: peptide -continued

```
    (ix) FEATURE:
         (A) NAME/KEY: Region
         (B) LOCATION: 1..9
         (D) OTHER INFORMATION: /note= "amino acid sequence of
              N-terminal region of sarcotoxin mature
              peptide"

(xi) SEQUENCE DESCRIPTION: SEQ ID NO:17:

Gly Trp Leu Lys Lys Ile Gly Lys Lys
1               5

(2) INFORMATION FOR SEQ ID NO:18:

(i) SEQUENCE CHARACTERISTICS:
         (A) LENGTH: 12 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..12
         (D) OTHER INFORMATION: /note= "amino acid sequence encoded by
              MSARCO51 primer"

(xi) SEQUENCE DESCRIPTION: SEQ ID NO:18:

His Ser Lys Arg Ala Gly Trp Leu Lys Lys Ile Gly
1               5                   10

(2) INFORMATION FOR SEQ ID NO:19:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: -
         (B) LOCATION: 1..24
         (D) OTHER INFORMATION: /note= "region of sarcotoxin gene
              encoding C-terminal of mature peptide"

(xi) SEQUENCE DESCRIPTION: SEQ ID NO:19:

GCTGCTACAG CCAGAGGTTA ATTG                                              24
```